United States Patent
Akagi et al.

(10) Patent No.: US 10,290,113 B2
(45) Date of Patent: May 14, 2019

(54) SURFACE STATE MONITORING APPARATUS FOR METALLIC BODY AND SURFACE STATE MONITORING METHOD FOR METALLIC BODY

(71) Applicant: NIPPON STEEL & SUMITOMO METAL CORPORATION, Tokyo (JP)

(72) Inventors: Toshio Akagi, Tokyo (JP); Yusuke Konno, Tokyo (JP); Hironao Yamaji, Tokyo (JP); Jun Umemura, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 201 days.

(21) Appl. No.: 15/514,311

(22) PCT Filed: Apr. 8, 2016

(86) PCT No.: PCT/JP2016/061490
§ 371 (c)(1),
(2) Date: Mar. 24, 2017

(87) PCT Pub. No.: WO2017/175367
PCT Pub. Date: Oct. 12, 2017

(65) Prior Publication Data
US 2018/0174316 A1    Jun. 21, 2018

(51) Int. Cl.
*H04N 7/18*    (2006.01)
*G06T 7/507*    (2017.01)
(Continued)

(52) U.S. Cl.
CPC .............. *G06T 7/507* (2017.01); *G01B 11/24* (2013.01); *G01B 11/30* (2013.01); *G01J 3/50* (2013.01);
(Continued)

(58) Field of Classification Search
CPC ........... G06T 7/507; G06T 7/40; G01B 11/24; G01B 11/30; G01J 3/50; G01N 21/892; G06F 17/11; H04N 7/18
(Continued)

(56) References Cited

U.S. PATENT DOCUMENTS 6,166,393 A    12/2000    Paul et al.
6,327,374 B1    12/2001    Piironen et al.
(Continued)

FOREIGN PATENT DOCUMENTS

DE    32 42 447 A1    5/1984
JP    4-294204 A    10/1992
(Continued)

OTHER PUBLICATIONS

Korean Reasons for Refusal, dated Jan. 26, 2018, for corresponding Korean Application No. 10-2017-7009798, with a partial English translation thereof.
(Continued)

*Primary Examiner* — Nguyen T Truong
(74) *Attorney, Agent, or Firm* — Birch, Stewart, Kolasch & Birch, LLP

(57) ABSTRACT

[Object] To monitor, on a metallic body surface, a region that has a specific hue and a region that does not have the specific hue and has a surface whose roughness varies.
[Solution] Included are: a measurement apparatus which includes a line sensor camera which is provided such that an optical axis of the line sensor camera is substantially parallel to a normal direction of a metallic body surface, and first, second, and third illumination light sources each configured to irradiate the metallic body surface with first, second, and third illumination light beams each having a strip shape, the measurement apparatus being configured to measure separately respective reflected light beams of the three illumi-
(Continued)

nation light beams that have been emitted; and an arithmetic processing apparatus configured to calculate surface state monitoring information on the basis of luminance values of the reflected light beams. The second and third illumination light sources are provided such that a second angle between an optical axis of the second illumination light source and the optical axis of the line sensor camera is substantially equal to a third angle between an optical axis of the third illumination light source and the optical axis of the line sensor camera, and the first illumination light source is provided such that a first angle between the optical axis of the line sensor camera and an optical axis of the first illumination light source is larger than the second angle. The arithmetic processing apparatus calculates information on a hue of the metallic body surface on the basis of a luminance value of the reflected light beam of the first illumination light beam and information on surface roughness of the metallic body on the basis of luminance values of the respective reflected light beams of the second and third illumination light beams.

14 Claims, 8 Drawing Sheets

(51) Int. Cl.
| | |
|---|---|
| *G01B 11/30* | (2006.01) |
| *G01N 21/892* | (2006.01) |
| *G01B 11/24* | (2006.01) |
| *G01J 3/50* | (2006.01) |
| *G06F 17/11* | (2006.01) |
| *G06T 7/40* | (2017.01) |

(52) U.S. Cl.
CPC ........... *G01N 21/892* (2013.01); *G06F 17/11* (2013.01); *G06T 7/40* (2013.01); *H04N 7/18* (2013.01)

(58) Field of Classification Search
USPC ........................................................ 348/135
See application file for complete search history.

(56) References Cited

U.S. PATENT DOCUMENTS

| | | |
|---|---|---|
| 2001/0015414 A1 | 8/2001 | Keranen et al. |
| 2010/0091272 A1 | 4/2010 | Asada et al. |

FOREIGN PATENT DOCUMENTS

| | | |
|---|---|---|
| JP | 2001-242091 A | 9/2001 |
| JP | 2001-514386 A | 9/2001 |
| JP | 2002-168791 A | 6/2002 |
| JP | 2004-138417 A | 5/2004 |
| JP | 2005-214720 A | 8/2005 |
| JP | 2008-202949 A | 9/2008 |
| KR | 10-2015-0094948 A | 8/2015 |

OTHER PUBLICATIONS

International Search Report for PCT/JP2016/061490 (PCT/ISA/210) dated Jul. 5, 2016.
Office Action issued in JP 2016-566295 dated Feb. 28, 2017.
Written Opinion of the International Searching Authority for PCT/JP2016/061490 (PCT/ISA/237) dated Jul. 5, 2016.
Extended European Search Report for corresponding European Application No. 16840307.9, dated Dec. 13, 2018.

US 10,290,113 B2

SURFACE STATE MONITORING APPARATUS FOR METALLIC BODY AND SURFACE STATE MONITORING METHOD FOR METALLIC BODY

TECHNICAL FIELD

The present invention relates to a surface state monitoring apparatus for a metallic body that monitors a surface state of a metallic body, and a surface state monitoring method for a metallic body.

BACKGROUND ART

As one of methods of measuring a surface state of a measurement target, there is given a method including using illumination light of a laser beam or the like and imaging reflected light of the illumination light reflected from the measurement target, and measuring the surface state of the measurement target. For example, in the case where the measurement target is a steel plate, measurement of the surface state is performed in order to monitor surface abnormalities that may degrade product quality.

The surface abnormalities to be measured include a minute surface abnormality that may be missed in a visual inspection on a video on a monitor, and a wide and large surface abnormality that can be monitored in a visual inspection during plate passing. Here, examples of the large surface abnormality include yellowing and a temper color, and there are many abnormalities that should be distinguished from each other. On the other hand, examples of the minute surface abnormality include rough skin in which surface roughness varies and scale residue. For monitoring separately those surface abnormalities, Patent Literature 1 discloses a method of inspecting flaws occurred on a steel plate, the method including irradiating a surface of the steel plate with first strip-shaped light and second strip-shaped light, the second strip-shaped light being white light, detecting minute flaws by imaging a reflected image of the first strip-shaped light in a gray image, detecting sheet flaws by imaging a reflected image of the second strip-shaped light in a color image having resolution lower than the resolution of the gray image, and determining a type of sheet flaws using hues.

CITATION LIST

Patent Literature

Patent Literature 1: JP 2004-138417A

SUMMARY OF INVENTION

Technical Problem

However, in Patent Literature 1, since the flaws other than the sheet flaws are detected in the gray image, in the case where a surface abnormality in which surface roughness varies appears within a region where a specific hue appears on the surface, for example, the contrast of the surface abnormality in which surface roughness varies is decreased, and the abnormality may not necessarily be detected.

Accordingly, the present invention has been made in the view of the above-mentioned problem, and an object of the present invention is to provide a surface state monitoring apparatus for a metallic body and a surface state monitoring method for a metallic body which are novel and improved, and which are capable of monitoring, on a surface of the metallic body, a region that has a specific hue and a region that does not have the specific hue and has a surface whose roughness varies.

Solution to Problem

According to an aspect of the present invention in order to solve the above-mentioned problem, there is provided a surface state monitoring apparatus for a metallic body, the surface state monitoring apparatus including: a measurement apparatus configured to irradiate a surface of a metallic body with three illumination light beams, and measure separately reflected light beams of the illumination light beams from the surface of the metallic body; and an arithmetic processing apparatus configured to calculate surface state monitoring information used for monitoring a surface state of the metallic body on the basis of luminance values of the reflected light beams measured by the measurement apparatus. The measurement apparatus includes a color line sensor camera configured to be capable of measuring separately reflected light beams of the illumination light beams from the surface of the metallic body, and a first illumination light source, a second illumination light source, and a third illumination light source each configured to irradiate the surface of the metallic body with strip-shaped illumination light. The color line sensor camera is provided in a manner that an optical axis of the color line sensor camera is substantially parallel to a normal direction of the surface of the metallic body. The second illumination light source and the third illumination light source are provided in a manner that a second angle between the optical axis of the color line sensor camera and an optical axis of the second illumination light source is substantially equal to a third angle between the optical axis of the color line sensor camera and an optical axis of the third illumination light source. The first illumination light source is provided in a manner that a first angle between the optical axis of the color line sensor camera and an optical axis of the first illumination light source is different from the second angle and the third angle. The arithmetic processing apparatus calculates, as the surface state monitoring information, first information on a hue of the surface of the metallic body and second information on surface roughness of the metallic body, on the basis of a luminance value of the reflected light beam of a first illumination light, a luminance value of the reflected light beam of a second illumination light, and a luminance value of the reflected light beam of a third illumination light, and determines the surface state of the metallic body on the basis of the first information on the hue of the surface of the metallic body and the second information on the surface roughness of the metallic body.

The first illumination light source, the second illumination light source, and the third illumination light source may be provided in a manner that the first angle is larger than the second angle and the third angle.

For a color of the first illumination light source, a color that is nearest to a complementary color of a hue measured at an abnormal portion of the surface of the metallic body may be selected from red, green, and blue, which are the primary colors of light, and for colors of the second illumination light source and the third illumination light source, two colors other than the color of the first illumination light source may be selected from red, green, and blue.

In this case, an angle between the optical axis of the color line sensor camera and the normal direction of the surface of the metallic body may be less than or equal to 5°, the first angle may be more than or equal to 45°, and the second angle and the third angle may each be more than or equal to 3° and less than or equal to 30°.

Further, the first illumination light source, the second illumination light source, and the third illumination light source may be provided in a manner that the first angle is smaller than the second angle and the third angle.

In this case, for a color of the first illumination light source, a color that is nearest to a hue measured at an abnormal portion of the surface of the metallic body may be selected from red, green, and blue, which are the primary colors of light, and for colors of the second illumination light source and the third illumination light source, two colors other than the color of the first illumination light source may be selected from red, green, and blue.

In this case, an angle between the optical axis of the color line sensor camera and the normal direction of the surface of the metallic body may be less than or equal to 5°, the first angle may be more than or equal to 3° and less than or equal to 30°, and the second angle and the third angle may be each more than or equal to 45°.

Colors of the first illumination light source, the second illumination light source, and the third illumination light source may be selected from red, green, and blue, which are the primary colors of light, and the colors of the first illumination light source, the second illumination light source, and the third illumination light source may be different from each other in a manner that a combination of the colors is any one of a combination in which the color of the first illumination light is red and a combination of the colors of the second illumination light and the third illumination light includes blue and green, a combination in which the color of the first illumination light is blue and the combination of the colors of the second illumination light and the third illumination light includes red and green, and a combination in which the color of the first illumination light is green and the combination of the colors of the second illumination light and the third illumination light includes red and blue.

Further, according to another aspect of the present invention in order to solve the above-mentioned problem, there is provided a surface state monitoring method for a metallic body, the method including: by using a measurement apparatus including a color line sensor camera configured to be provided in a manner that an optical axis of the color line sensor camera is substantially parallel to a normal direction of a surface of a metallic body and configured to be capable of measuring separately reflected light beams of illumination light beams from the surface of the metallic body, and a first illumination light source, a second illumination light source, and a third illumination light source each configured to irradiate the surface of the metallic body with strip-shaped illumination light, irradiating the surface of the metallic body with illumination light beams, by the second illumination light source and the third illumination light source which are provided in a manner that a second angle between the optical axis of the color line sensor camera and an optical axis of the second illumination light source is substantially equal to a third angle between the optical axis of the color line sensor camera and an optical axis of the third illumination light source, and the first illumination light source which is provided in a manner that a first angle between the optical axis of the color line sensor camera and an optical axis of the first illumination light source is different from the second angle and the third angle, and measuring separately reflected light beams of the illumination light beams from the surface of the metallic body; calculating, by an arithmetic processing apparatus configured to calculate surface state monitoring information used for monitoring a surface state of the metallic body on the basis of luminance values of the reflected light beams measured by the measurement apparatus, as the surface state monitoring information, first information on a hue of the surface of the metallic body and second information on surface roughness of the metallic body, on the basis of a luminance value of the reflected light beam of a first illumination light, a luminance value of the reflected light beam of a second illumination light, and a luminance value of the reflected light beam of a third illumination light; and determining the surface state of the metallic body on the basis of the first information on the hue of the surface of the metallic body and the second information on the surface roughness of the metallic body.

Advantageous Effects of Invention

According to the present invention, as described above, it becomes possible to monitor, on the surface of the metallic body, a region that has a specific hue and a region that does not have the specific hue and has a surface whose roughness varies.

DESCRIPTION OF EMBODIMENTS

Figure 1:
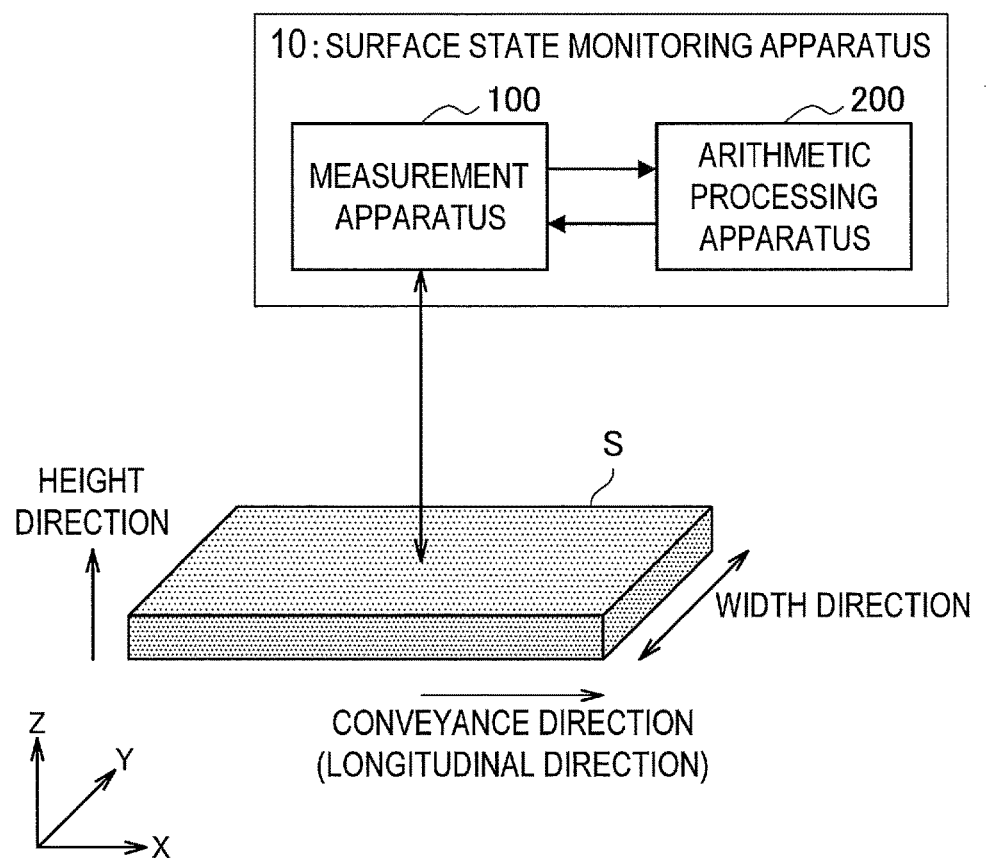
FIG. 1 is an explanatory view showing a configuration example of a surface state monitoring apparatus according to a first embodiment of the present invention.

Hereinafter, (a) preferred embodiment(s) of the present invention will be described in detail with reference to the appended drawings. In this specification and the appended drawings, structural elements that have substantially the same function and structure are denoted with the same reference numerals, and repeated explanation of these structural elements is omitted.

1. First Embodiment

[1-1. Outline of Surface State Monitoring Apparatus]

First, with reference to FIG. 1, there will be described an outline of a surface state monitoring apparatus for a metallic body (hereinafter, also simply referred to as "surface state monitoring apparatus") 10 according to a first embodiment of the present invention. FIG. 1 is an explanatory view showing a configuration example of the surface state monitoring apparatus 10 according to the present embodiment. Note that, in the following description, a metallic body S is assumed to be conveyed in a predetermined direction on a conveyor line (not shown), and a conveyance direction of the metallic body S is assumed to correspond to the longitudinal direction of the metallic body S.

The surface state monitoring apparatus 10 according to the present embodiment is an apparatus that monitors the surface states (for example, hues and surface roughness) of various metallic bodies S, such as a steel plate placed at a predetermined location and a steel plate conveyed on a predetermined conveyor line.

Here, a macroscopic shape of the metallic body S is not particularly limited and may be, for example, a plate shape such as a slab or a billet, or a coil shape in which a metal plate is wound up. Components of the metallic body S are also not particularly limited, and the metallic body S may be various types of steel containing an iron element as the main component, various types of alloy of iron and other metal elements, or various types of nonferrous metal.

The surface state monitoring apparatus 10 according to the present embodiment mainly includes, as shown in FIG. 1, a measurement apparatus 100 and an arithmetic processing apparatus 200.

Under control of the arithmetic processing apparatus 200, the measurement apparatus 100 irradiates the metallic body S (specifically, the surface of the metallic body S) with three illumination light beams, and measures separately reflected light beams from the metallic body S (specifically, the surface of the metallic body S) of the illumination light beams to generate data on luminance values of the reflected light beams. The measurement apparatus 100 outputs the generated data on the luminance values of the reflected light beams to the arithmetic processing apparatus 200.

The arithmetic processing apparatus 200 controls a measurement process of the metallic body S performed by the measurement apparatus 100. In addition, the arithmetic processing apparatus 200 acquires the data on the luminance values of the reflected light beams generated by the measurement apparatus 100, and performs data processing on the acquired data on the luminance values, thereby calculating various types of information used for monitoring the surface state of the metallic body S. Examples of the surface state of the metallic body S include a hue and surface roughness of the metallic body S. In the following description, various types of information used for monitoring the surface state of the metallic body S are collectively referred to as "surface state monitoring information". Examples of the surface state monitoring information calculated by the arithmetic processing apparatus 200 include information on a hue of the surface of the metallic body S, and information on surface roughness of the metallic body S.

The measurement process of the metallic body S performed by the measurement apparatus 100 and a calculation process of the surface state monitoring information performed by the arithmetic processing apparatus 200 can be performed in real time along with conveyance of the metallic body S. A user of the surface state monitoring apparatus 10 can recognize and monitor in real time the surface state of the metallic body S by focusing on monitoring results output from the surface state monitoring apparatus 10 (specifically, the arithmetic processing apparatus 200). In addition, the surface state of the metallic body S can be determined automatically by the surface state monitoring apparatus 10 on the basis of the calculated surface state monitoring information. Hereinafter, each of the measurement apparatus 100 and the arithmetic processing apparatus 200 will be described in detail.

[1-2. Configuration of Surface State Monitoring Apparatus]

(a) Measurement Apparatus

Figure 2:
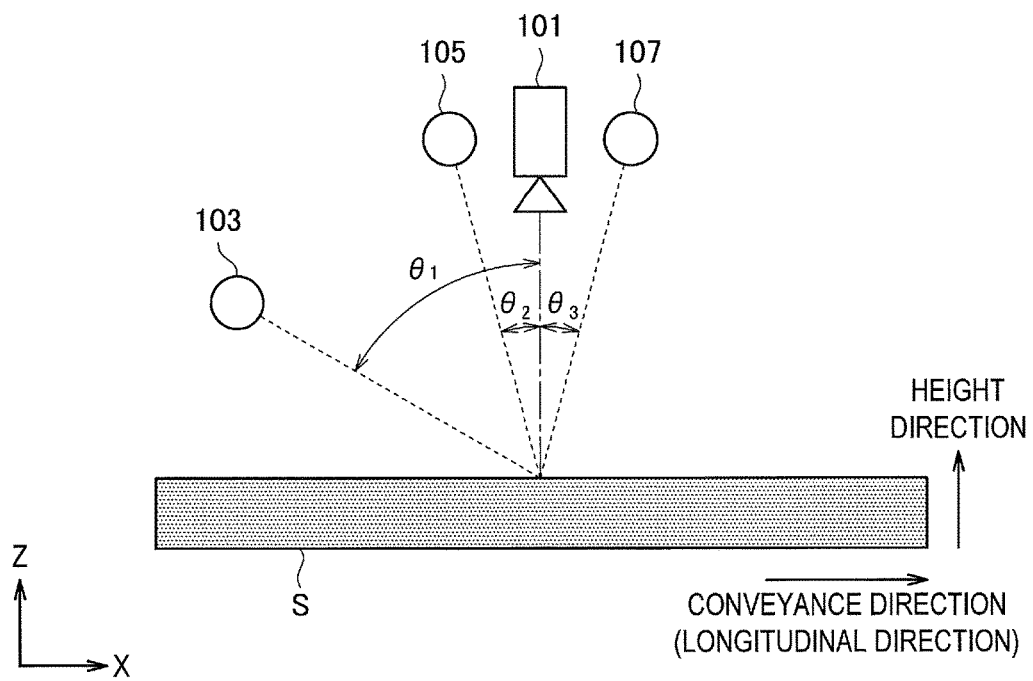
FIG. 2 is an explanatory view schematically showing a configuration example of a measurement apparatus included in the surface state monitoring apparatus according to the embodiment, and shows a state in which a metallic body is viewed from a side face.
Figure 3:
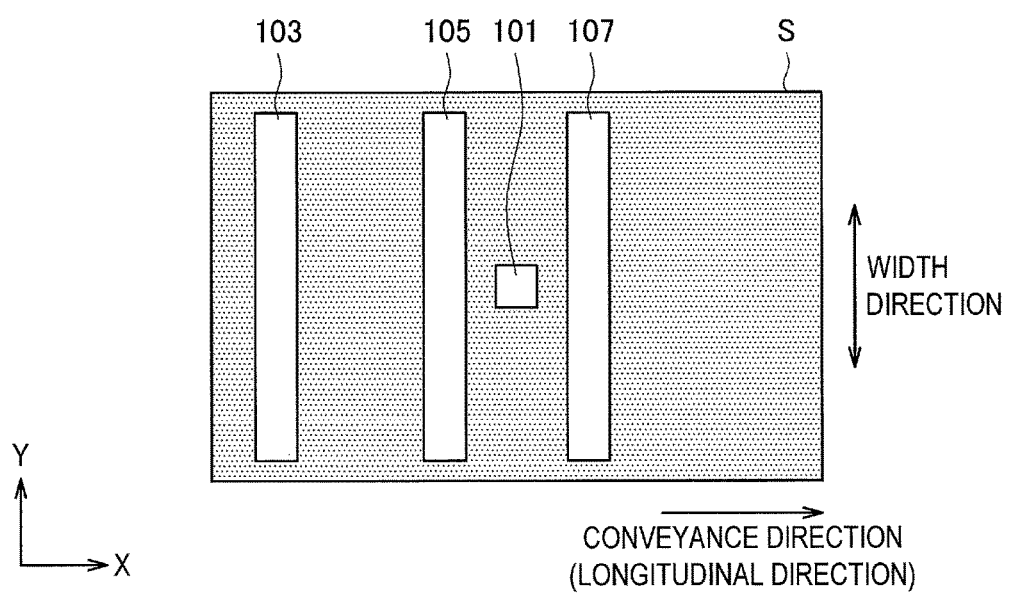
FIG. 3 is a plan view of FIG. 2.

First, with reference to FIGS. 2 and 3, the measurement apparatus 100 according to the present embodiment will be described in detail. Note that FIG. 2 is an explanatory view schematically showing a configuration example of the measurement apparatus 100 included in the surface state monitoring apparatus 10 according to the present embodiment, and shows a state in which the metallic body S is viewed from a side face. FIG. 3 is a plan view of FIG. 2.

The measurement apparatus 100 according to the present embodiment includes, as shown in FIGS. 2 and 3, a color line sensor camera 101, a first illumination light source 103, a second illumination light source 105, and a third illumination light source 107. The color line sensor camera 101, the first illumination light source 103, the second illumination light source 105, and the third illumination light source 107 are fixed with a known method in a manner that the setting positions are stationary.

(Color Line Sensor Camera)

The color line sensor camera 101 is an imaging apparatus that images an image on a one-dimensional line basis. As the color line sensor camera 101, a known 3CCD color line sensor camera can be used, for example. The color line sensor camera 101 can individually and simultaneously measure magnitudes of various wavelength components (for example, an R component, a G component, and a B component) included in reflected light beams of a first illumination light beam, a second illumination light beam, and a third illumination light beam. Note that, regarding the wavelength components, the R component (red component) represents a component corresponding to light having a wavelength of 600 to 700 nm, the G component (green component) represents a component corresponding to light having a wavelength of 500 to 560 nm, and the B component (blue component) represents a component corresponding to light having a wavelength of 430 to 500 nm, for example.

The color line sensor camera 101 is provided in a manner that the optical axis of the color line sensor camera 101 is perpendicular to the surface of the metallic body S (hereinafter, also referred to as "metallic body surface"), above the metallic body S (side in the positive direction of the Z-axis). The color line sensor camera 101 measures separately reflected light beams of the first illumination light beam emitted from the first illumination light source 103, the second illumination light beam emitted from the second illumination light source 105, and the third illumination light beam emitted from the third illumination light source 107, which are reflected on the metallic body surface. In this way, the color line sensor camera 101 can specify data indicating intensities of reflected light beams of the first illumination light beam, the second illumination light beam, and the third illumination light beam reflected on the metallic body surface (that is, data indicating luminance values of the reflected light beams). As a result of the color line sensor camera 101 imaging the metallic body surface every time the metallic body S is conveyed a certain distance, for example, the color line sensor camera 101 can specify distribution in a conveyance direction and a width direction (in the XY-plane of FIG. 1) of each of the reflected light of the first illumination light on the metallic body surface, the reflected light of the second illumination light on the metallic body surface, and the reflected light of the third illumination light on the metallic body surface.

The color line sensor camera 101 measures separately the respective luminance values of the reflected light beams of the first illumination light beam, the second illumination light beam, and the third illumination light beam, generates data corresponding to the acquired measurement results (data on the luminance values of the reflected light beams), and outputs the data to the arithmetic processing apparatus 200 to be described later.

(Illumination Light Source)

The measurement apparatus 100 according to the present embodiment includes three illumination light sources, the first illumination light source 103, the second illumination light source 105, and the third illumination light source 107. The illumination light sources 103, 105, and 107 irradiate the surface of the metallic body S with the first illumination light, the second illumination light, and the third illumination light, respectively. The respective central wavelengths of the first illumination light, the second illumination light, and the third illumination light are different from each other. The intensities (luminance values) of those illumination light beams can be measured separately by the color line sensor camera 101. By making it possible to measure separately the first illumination light, the second illumination light, and the third illumination light, it becomes possible to easily specify which one of the first illumination light, the second illumination light, and the third illumination light, the distribution of the luminance value of the reflected light that the color line sensor camera 101 has measured corresponds to.

The first illumination light source 103, the second illumination light source 105, and the third illumination light source 107 are set, as shown in FIG. 3, for example, so as to be able to irradiate substantially entire area of the metallic body S in the width direction with the illumination light. In such a setting any light source can be used as the first illumination light source 103, the second illumination light source 105, and the third illumination light source 107. For example, each illumination light source may be a rod-like LED light, or may be a laser beam expanded by a rod lens or the like into a linear shape. Moreover, as a visible-light light source used as the first illumination light source 103, the second illumination light source 105, and the third illumination light source 107, a single-wavelength laser beam or an LED may be used, or a light source with a continuous spectrum may be used.

The first illumination light source 103 is provided for acquiring first information on a hue of the metallic body surface. As a surface abnormality that occurs on the metallic body surface, there is a case where variation in hue occurs widely on the metallic body surface. Examples of such a surface abnormality include yellowing that occurs during a process of pickling a steel plate, and a temper color that occurs in a process of producing a stainless steel plate. For the first illumination light source 103, it is desirable to provide the following light source for monitoring with high sensitivity the variation in hue that occurs widely on the metallic body surface.

First, the wavelength of the first illumination light source 103 is selected from the wavelength band range corresponding to a complementary color of a hue monitored from the metallic body surface. In this way, the variation in hue that occurs on the metallic body surface can be monitored with high accuracy.

Further, the first illumination light source 103 is disposed in a manner that the illumination light is incident on the metallic body surface at a low angle. That is, the first illumination light source 103 is provided in a manner that an angle (first angle: $\theta_1$) between the optical axis of the first illumination light source 103 and the optical axis of the color line sensor camera 101 is more than or equal to 45°. Note that the angle $\theta_1$ is set to an angle larger than an angle (second angle: $\theta_2$) between the optical axis of the second illumination light source 105 to be described later and the optical axis of the color line sensor camera 101 and an angle (third angle: $\theta_3$) between the optical axis of the third illumination light source 107 to be described later and the optical axis of the color line sensor camera 101.

By providing the first illumination light source 103 in this manner, the color line sensor camera 101 measures the reflected light of the illumination light emitted from the first illumination light source 103 at a position distant from a specular direction. Accordingly, the color line sensor camera 101 acquires the reflected light of the first illumination light as diffused reflection measurement data having a small amount of the specular reflection component. Since the data measured at a position distant from the specular reflection exhibits a color density (that is, chroma) strongly, the contrast in the image can be increased, and as a result, the sensitivity of the monitoring of hue variation can be increased.

On the other hand, the second illumination light source 105 and the third illumination light source 107 are provided for acquiring second information on surface roughness of the metallic body S. On the metallic body surface, there are regions which does not have a specific hue and in which the surface roughness varies, such as rough skin that occurs due to overpickling during a pickling process and scale residue that occurs due to insufficient pickling. For the second illumination light source 105 and the third illumination light source 107, it is desirable to provide the following light sources for monitoring with high sensitivity the variation in surface roughness on the metallic body surface.

First, the wavelengths of the second illumination light source 105 and the third illumination light source 107 are selected from the wavelength band range other than the wavelength band range of the first illumination light source 103. In this case, the wavelength of the second illumination light source 105 and the wavelength of the third illumination light source 107 are different from each other.

Further, the second illumination light source 105 and the third illumination light source 107 are disposed in a manner that the illumination light beams are incident on the metallic body surface at high angles. To be specific, as shown in FIG. 2, the second illumination light source 105 and the third illumination light source 107 are provided symmetrically about the optical axis of the color line sensor camera 101. That is, where an angle (second angle) between the optical axis of the second illumination light source 105 and the optical axis of the color line sensor camera 101 is represented by $\theta_2$, and an angle (third angle) between the optical axis of the third illumination light source 107 and the optical axis of the color line sensor camera 101 is represented by $\theta_3$, the second angle $\theta_2$ and the third angle $\theta_3$ are substantially equal to each other.

Here, the angular difference $|\theta_2 - \theta_3|$ between the second angle $\theta_2$ and the third angle $\theta_3$ is preferably less than or equal to 10°, for example. With the angular difference within such a range, there can be obtained easily an image hardly influenced by variation in hue that occurs in the metallic body surface.

In this case, in order that the second illumination light and the third illumination light are measured in near-specular reflection states, the second illumination light source 105 and the third illumination light source 107 are provided in a manner that the degrees of angles between the optical axis of the second illumination light source 105 and the optical axis of the color line sensor camera 101 and between the optical axis of the third illumination light source 107 and the optical axis of the color line sensor camera 101, respectively, are as small as possible as long as there is no constraint on light sources installation. For example, the second angle $\theta_2$ and the third angle $\theta_3$ are each set to more than or equal to 3° and less than or equal to 30°. In this way, the color line sensor camera 101 can acquire the reflected light of the second illumination light and the reflected light of the third illumination light as specular reflection measurement data that is near the specular reflection. Since the data measured under the condition near the specular reflection clearly exhibits variation in surface roughness on the metallic body, the variation in surface roughness can be monitored with high sensitivity.

The color line sensor camera 101, the first illumination light source 103, the second illumination light source 105, and the third illumination light source 107 are provided as shown in FIG. 2 and FIG. 3, and thus, the state of the metallic body surface can be monitored. That is, in the case where there is variation in the hue on the metallic body surface, variation occurs in the luminance value of the reflected light of the first illumination light. Further, with the reflected light of the second illumination light and the reflected light of the third illumination light, variation in surface roughness can be monitored with high sensitivity in a state hardly influenced by variation in hue on the metallic body surface.

Heretofore, the configuration of the measurement apparatus 100 according to the present embodiment has been described. Although the case has been described in FIG. 2 and FIG. 3 in which the first illumination light source 103 and the second illumination light source 105 are provided on the upstream side of the conveyance direction, and the third illumination light source 107 is provided on the downstream side of the conveyance direction, the present invention is not limited to such an example. For example, the third illumination light source 107 may be provided on the upstream side of the conveyance direction and the first illumination light source 103 and the second illumination light source 105 may be provided on the downstream side of the conveyance direction.

(b) Arithmetic Processing Apparatus

Figure 4:
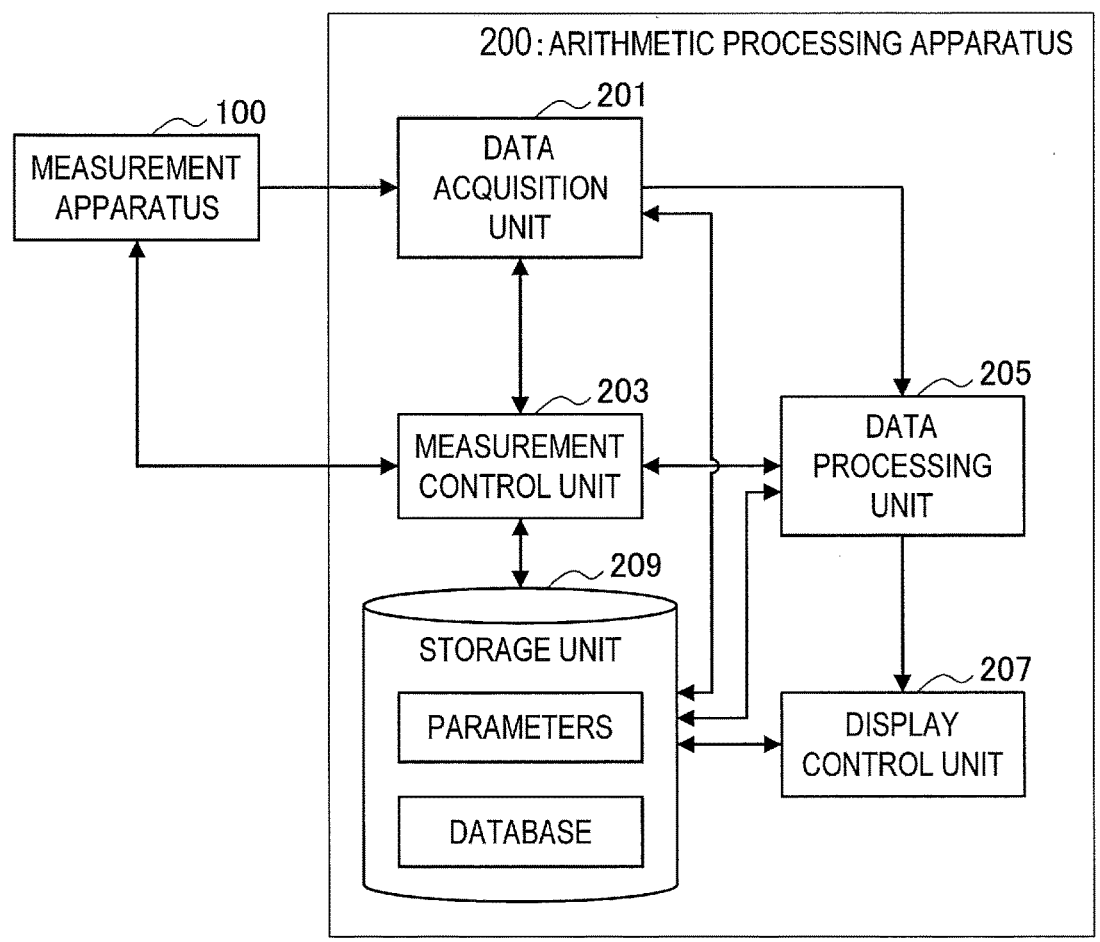
FIG. 4 is a block diagram showing an example of an overall configuration of an arithmetic processing apparatus according to the embodiment.
Figure 5:
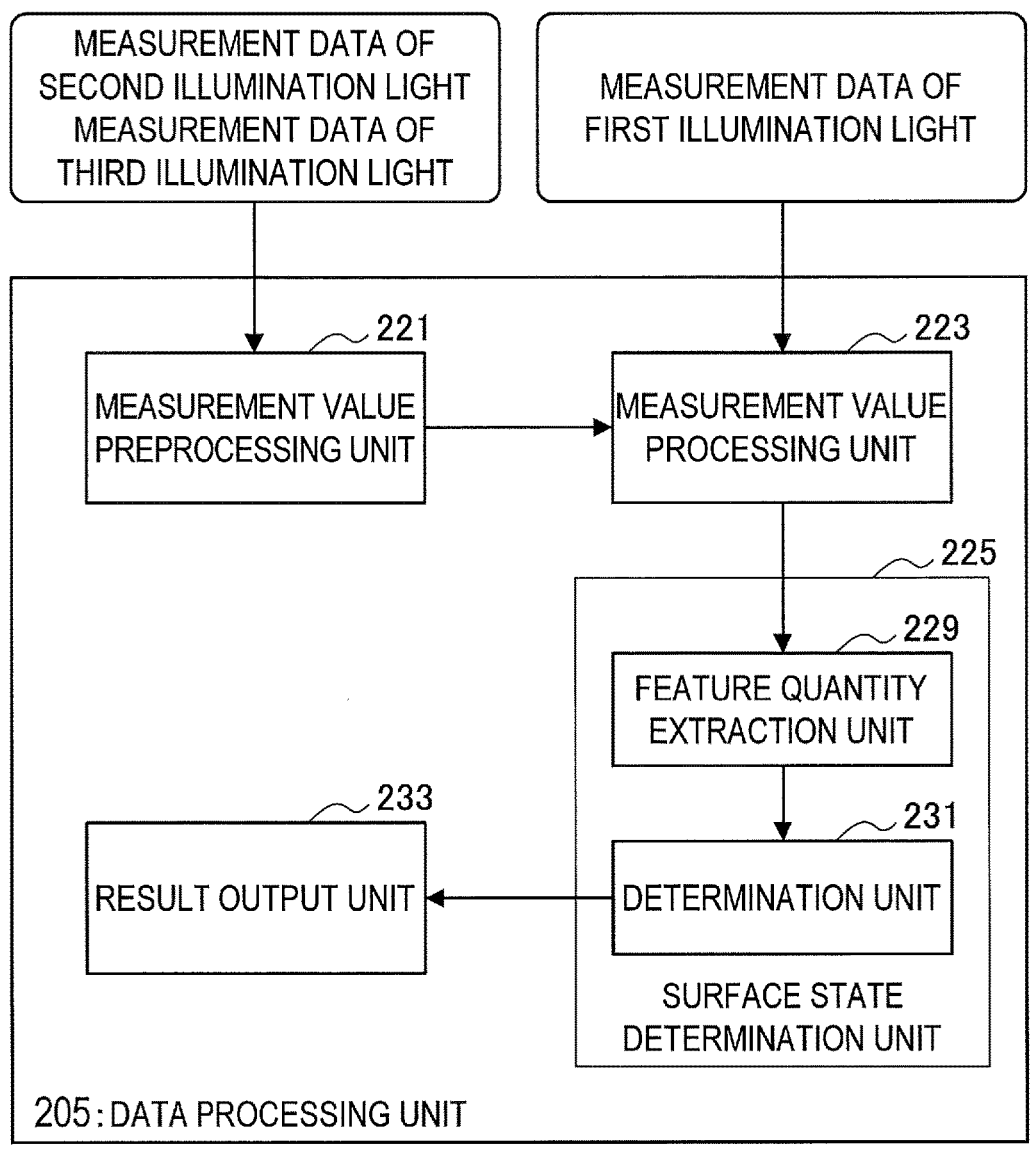
FIG. 5 is a block diagram showing an example of a configuration of a data processing unit according to the embodiment.

Next, with reference to FIG. 4 and FIG. 5, there will be described in detail a configuration of the arithmetic processing apparatus 200 included in the surface state monitoring apparatus 10 according to the present embodiment. Note that FIG. 4 is a block diagram showing an example of an overall configuration of the arithmetic processing apparatus 200 according to the present embodiment. FIG. 5 is a block diagram showing an example of a configuration of a data processing unit 205 according to the present embodiment.

The arithmetic processing apparatus 200 according to the present embodiment is an apparatus that calculates surface state monitoring information used for monitoring a surface state of the metallic body S on the basis of luminance values of the reflected light beams measured by the measurement apparatus 100. The arithmetic processing apparatus 200 calculates, as the surface state monitoring information, at least first information on a hue of the surface of the metallic body and second information on surface roughness of the metallic body.

As shown in FIG. 4, the arithmetic processing apparatus 200 mainly includes a data acquisition unit 201, a measurement control unit 203, a data processing unit 205, a display control unit 207, and a storage unit 209.

(Data Acquisition Unit)

The data acquisition unit 201 is configured with, for example, a central processing unit (CPU), a read only memory (ROM), a random access memory (RAM), and a communication device. The data acquisition unit 201 acquires data on luminance values of reflected light, which is generated and output by the measurement apparatus 100, and transmits the data to the data processing unit 205 described later. Moreover, the data acquisition unit 201 may contain the acquired data on the luminance values of the reflected light as history information in the storage unit 209 described later, in association with time information on date and time at which the data is acquired.

(Measurement Control Unit)

The measurement control unit 203 is configured with a CPU, a ROM, a RAM, a communication device, and the like. The measurement control unit 203 controls measurement of the metallic body S performed by the measurement apparatus 100 according to the present embodiment. Specifically, in starting the measurement of the metallic body S, the measurement control unit 203 sends control signals for starting emission of illumination light beams to the first illumination light source 103, the second illumination light source 105, and the third illumination light source 107.

When the first illumination light source 103, the second illumination light source 105, and the third illumination light source 107 start to irradiate the surface of the metallic body S with the respective illumination light beams, the measurement control unit 203 sends a trigger signal for starting measurement to the color line sensor camera 101, on the basis of a PLG signal that is sent at regular intervals from a driving mechanism and the like for changing a relative position between the metallic body S and the measurement apparatus 100 (for example, a PLG signal output each time the metallic body S moves 1 mm).

In this manner, the measurement apparatus 100 can generate measurement data (data on luminance values of reflected light) at each position of the metallic body S in the conveyance direction.

(Data Processing Unit)

The data processing unit 205 is configured with, for example, a CPU, a ROM, a RAM, and a communication device. The data processing unit 205 uses data on luminance values of reflected light, generated by the measurement apparatus 100, to perform data processing, which will be described later, on the data on the luminance values of the respective reflected light beams, and calculates the surface state monitoring information used for monitoring the surface state of the metallic body S.

To describe in more detail the data processing unit 205 according to the present embodiment, as shown in FIG. 5, the data processing unit 205 includes a measurement value preprocessing unit 221, a measurement value processing unit 223, a surface state determination unit 225, and a result output unit 233.

The measurement value preprocessing unit 221 is a processing unit that calculates the sum of a luminance value of the reflected light of the second illumination light and a luminance value of the reflected light of the third illumination light, and is configured with a CPU, a ROM, a RAM, and the like. The measurement value preprocessing unit 221 multiplies at least one of data on a measurement value of the reflected light of the second illumination light acquired by the data acquisition unit 201 (hereinafter, referred to as "measurement data of the second illumination light") and data on a measurement value of the reflected light of the third illumination light (hereinafter, referred to as "measurement data of the third illumination light") by a predetermined coefficient, and calculates the sum of the measurement data of the second illumination light and the measurement data of the third illumination light.

Here, for the above coefficient, a value of a constant may be determined in advance in a manner that the difference is the smallest between: the value of the sum of the measurement data of the second illumination light and the measurement data of the third illumination light measured at a region in which an abnormal portion having a specific hue occurs on the metallic body S; and the value of the sum of the measurement data of the second illumination light and the measurement data of the third illumination light measured at a region in which the abnormal portion does not occur.

The data to be multiplied by the above coefficient may be the measurement data of the second illumination light, may be the measurement data of the third illumination light, and may be both of the measurement data of the second illumination light and the measurement data of the third illumination light.

To describe more specifically, as a matter of convenience, where the measurement data of the second illumination light is represented by $D_2$ and the measurement data of the third illumination light is represented by $D_3$, the measurement value preprocessing unit 221 may perform preprocessing calculation of $(D_1+k_a\times D_2)$ or $(k_a\times D_2+D)$, or may perform preprocessing calculation of $(k_b\times D_1+D_2)$ or $(D_2+k_b\times D_1)$. Note that the coefficients $k_a$ and $k_b$ are determined in advance, as described above, and are stored in the storage unit 209 and the like. Alternatively, the measurement value preprocessing unit 221 may perform preprocessing calculation of $(k_c\times D_1+k_d\times D_2)$ or $(k_d\times D_2+k_c\times D_1)$. The coefficients $k_c$ and $k_d$ are determined in advance in the same manner, as described above, and are stored in the storage unit 209 and the like.

By performing the preprocessing calculation involving calculating the sum after the multiplication of (a) predetermined coefficient(s), the measurement value preprocessing unit 221 can obtain a data group of values of sums of the entire surface of the metallic body S (that is, a map data on values of sums). The thus obtained data group of values of sums becomes a monitoring process target image (hereinafter, also referred to as "image for monitoring roughness variation") used for monitoring variation in surface roughness as a surface state of the metallic body S. The measurement value preprocessing unit 221 outputs the thus obtained data group of values of sums (image for monitoring roughness variation) to the measurement value processing unit 223.

By performing, by the measurement value preprocessing unit 221, preprocessing on the above-mentioned measurement value(s), variations in surface roughness can be measured with high accuracy also in the region in which an abnormal portion having a specific hue occurs.

The measurement value processing unit 223 refers to a data group of data on measurement values of the reflected light of the first illumination light (hereinafter, referred to as "measurement data of the first illumination light") and the data group of values of sums (the image for monitoring roughness variation) calculated by the measurement value preprocessing unit 221, and performs predetermined image processing on those data groups. The measurement value processing unit 223 is configured with a CPU, a ROM, a RAM, and the like.

The data group of the measurement data of the first illumination light becomes a monitoring process target image (hereinafter, also referred to as "image for monitoring hue variation") used for monitoring variation in hue on the metallic body surface as a surface state of the metallic body S. The measurement value processing unit 223 performs predetermined image processing on the image for monitoring hue variation and the image for monitoring roughness variation, which is calculated by the measurement value preprocessing unit 221, and outputs the processed data of the respective images to the surface state determination unit 225. Note that various parameter values used during the image processing are not particularly limited, and, for example, may be determined appropriately by analyzing operation data in the past and the like.

The surface state determination unit 225 determines the surface state of the metallic body S on the basis of the processed data of the image for monitoring hue variation and the image for monitoring roughness variation output by the measurement value processing unit 223. The surface state determination unit 225 is configured with a CPU, a ROM, a RAM, and the like.

The surface state determination unit 225 includes, as shown in FIG. 5, a feature quantity extraction unit 229 and a determination unit 231, and with cooperative functioning of those processing units, the surface state of the metallic body S is determined from the processed data. The contents of the processing performed by those processing units are not particularly limited, and a method for known surface state determination processing can be applied.

The feature quantity extraction unit 229 extracts, from the processed data of the image for monitoring hue variation and the image for monitoring roughness variation output from the measurement value processing unit 223, a known feature quantity that characterizes variation in the images, such as an average value or a dispersion value of each given range. The feature quantity extraction unit 229 outputs the extracted feature quantity to the determination unit 231.

The determination unit 231 refers to a database or the like indicating a correspondence relationship between a type of surface abnormality and a feature quantity, which is stored in the storage unit 209 in advance, and determines whether a surface abnormality is present in the processing region.

The determination unit 231 detects abnormalities present on the surface of the metallic body S, and for each detected surface abnormality, can specify a degree of harmfulness of the surface abnormality, for example. The determination unit 231 outputs a determination result of the surface abnormality to the result output unit 233.

The result output unit 233 outputs, to the display control unit 207, information on the determination result of the surface abnormality output from the determination unit 231. In this way, the information on abnormalities present on the surface of the metallic body S is output on a display unit (not shown). Further, the result output unit 233 may output the obtained determination result to an external device such as a process computer system for production management, and may create record files on abnormalities in products by utilizing the obtained determination results. Moreover, the result output unit 233 may contain information on the determination results of the surface abnormality, as history information, in the storage unit 209 or the like, in association with time information on date and time at which the information is calculated.

Upon ending the calculation process of surface state determination information, the data processing unit 205 having the above functions transmits information on the obtained processing results to the display control unit 207.

(Display Control Unit)

The display control unit 207 is configured with, for example, a CPU, a ROM, a RAM, and an output device. The display control unit 207 performs display control in displaying various processing results including calculation results of surface state determination information on the metallic body S, which are transmitted from the data processing unit 205, on an output device such as a display included in the arithmetic processing apparatus 200, an output device provided outside the arithmetic processing apparatus 200, or the like. Thus, a user of the surface state monitoring apparatus 10 can recognize on-site various processing results, such as surface state determination information on the metallic body S.

(Storage Unit)

The storage unit 209 is configured with, for example, a RAM and a storage device included in the arithmetic processing apparatus 200 according to the present embodiment. In the storage unit 209, various parameters and process intermediate progresses that the arithmetic processing apparatus 200 according to the present embodiment needs to save when performing some sort of process, various databases and programs, or the like are recorded as appropriate. With regard to this storage unit 209, the data acquisition unit 201, the measurement control unit 203, the data processing unit 205, the display control unit 207, and the like can perform a data read/write process freely.

An example of the function of the arithmetic processing apparatus 200 according to the present embodiment has been shown. Each of the above structural elements may be configured with a general-purpose member or circuit, and may be configured with hardware specialized for the function of each structural element. A CPU or the like may perform all of the functions of respective structural elements. Thus, a utilized configuration can be changed as appropriate, according to the technology level at the time of performing the present embodiment.

Note that the computer program for providing each function of the arithmetic processing apparatus according to the above present embodiment can be created and implemented in a personal computer or the like. Moreover, a computer-readable recording medium that contains this computer program can be provided as well. For example, the recording medium is a magnetic disk, an optical disc, a magneto-optical disk, a flash memory, or the like. The above computer program may be delivered via a network for example, without using the recording medium.

[1-3. Surface State Monitoring Method]

Figure 6:
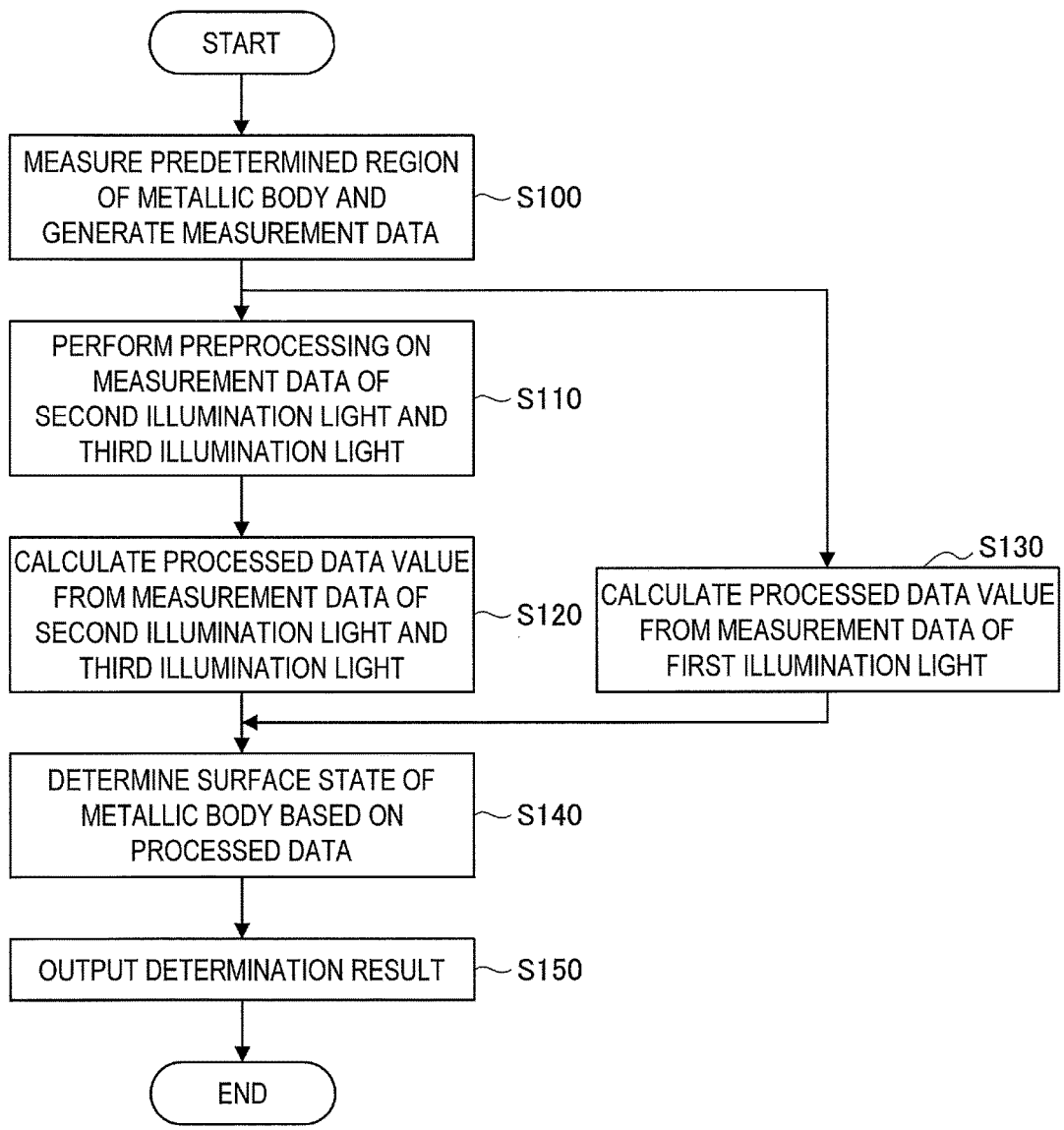
FIG. 6 is a flowchart showing an example of a surface state monitoring method according to the embodiment.

With reference to FIG. 6, there will be described an example of a surface state monitoring method executed in the surface state monitoring apparatus 10 according to the present embodiment. Note that FIG. 6 is a flowchart showing an example of a surface state monitoring method according to the present embodiment.

In the surface state monitoring method executed by the surface state monitoring apparatus 10 according to the present embodiment, under the control of measurement control unit 203 of the arithmetic processing apparatus 200, the measurement apparatus 100 irradiates a predetermined region on a surface of the metallic body S with three illumination light beams, and generates pieces of measurement data on the respective illumination light beams (Step S100). The measurement apparatus 100 generates and outputs to the arithmetic processing apparatus 200 the measurement data of the first illumination light, the measurement data of the second illumination light, and the measurement data of the third illumination light.

Next, the data acquisition unit 201 of the arithmetic processing apparatus 200 acquires the pieces of measurement data output from the measurement apparatus 100, and outputs, out of the acquired pieces of measurement data, the measurement data of the second illumination light and the measurement data of the third illumination light to the measurement value preprocessing unit 221 of the data processing unit 205. The data processing unit 205 receives the input of the measurement data of the second illumination light and the measurement data of the third illumination light, and the measurement value preprocessing unit 221 performs preprocessing of calculating the sum of the pieces of measurement data (Step S110).

In Step S110, as described above, processing of multiplying at least one of the measurement data of the second illumination light and the measurement data of the third illumination light by a predetermined coefficient, and calculating the sum of the measurement data of the second illumination light and the measurement data of the third illumination light. The measurement value preprocessing unit 221 outputs a data group of obtained values of sums to the measurement value processing unit 223 of the data processing unit 205.

The measurement value processing unit 223 performs predetermined processing on the data group of values of sums (image for monitoring roughness variation) that is data after the preprocessing, which is calculated in Step S110, and on a data group of the measurement data of the first illumination light (image for monitoring hue variation) that is diffused reflection measurement data (Step S120, S130). The measurement value processing unit 223 processes the image for monitoring roughness variation and calculates processed data for specifying a candidate region in which roughness variation occurs (Step S120). Further, the measurement value processing unit 223 processes the image for monitoring hue variation and calculates processed data for specifying a candidate region in which hue variation occurs (Step S130). The measurement value processing unit 223 outputs those pieces of processed data to the surface state determination unit 225.

Then, the feature quantity extraction unit 229 and the determination unit 231 included in the surface state determination unit 225 each execute the above-mentioned known surface abnormality monitoring processing on the pieces of processed data (Step S140). The image for monitoring hue variation is an image based on diffused reflection measurement data, and from the image, a region in which hue variation occurs on the metallic body surface can be specified. On the other hand, the image for monitoring roughness variation is an image based on specular reflection measurement data, and from the image, a region in which roughness varies on the metallic body surface can be specified. In this case, the image for monitoring hue variation and the image for monitoring roughness variation do not influence each other, and abnormalities on the metallic body surfaces that appear in the respective images can be monitored. The surface state determination unit 225 outputs, through the determination unit 231, the obtained determination result to the result output unit 233.

After that, the result output unit 233 outputs data indicating the determination results of the surface state input by the surface state determination unit 225 to a user or externally provided devices (Step S150). In this way, the user can grasp the results of monitoring the surface state of the metallic body S.

[1-4. Conclusion]

Heretofore, the configuration of the surface state monitoring apparatus 10 according to the first embodiment of the present invention and the surface state monitoring method performed by the surface state monitoring apparatus 10 have been described. According to the present embodiment, the surface of the metallic body S is irradiated with three illumination light beams and the color line sensor camera 101, which is provided so as to be substantially parallel to a normal direction of the surface of the metallic body S, measures separately reflected light beams of the respective illumination light beams.

Here, the first illumination light source 103 is a light source that emits light of a wavelength belonging to a wavelength band range corresponding to a complementary color of a hue measured from a surface abnormal portion of the metallic body, and is provided in a manner that the illumination light is incident on the metallic body surface at a low angle. Such a first illumination light source 103 is provided in the above-mentioned manner, and hence, the first information on a hue of the surface of the metallic body S can be acquired from the measurement data of the first illumination light acquired by the color line sensor camera 101.

Further, the second illumination light source 105 and the third illumination light source 107 are each a light source that emits light of a wavelength belonging to a wavelength band range corresponding to a hue monitored from the metallic body surface using the first illumination light source 103, and are provided in a manner that the illumination light beams are incident on the metallic body surface at high angles. Such second illumination light source 105 and third illumination light source 107 are provided in the above-mentioned manner, and hence, the second information on surface roughness of the metallic body S can be acquired from the measurement data of the second illumination light and the measurement data of the third illumination light acquired by the color line sensor camera 101.

2. Second Embodiment

Figure 7:
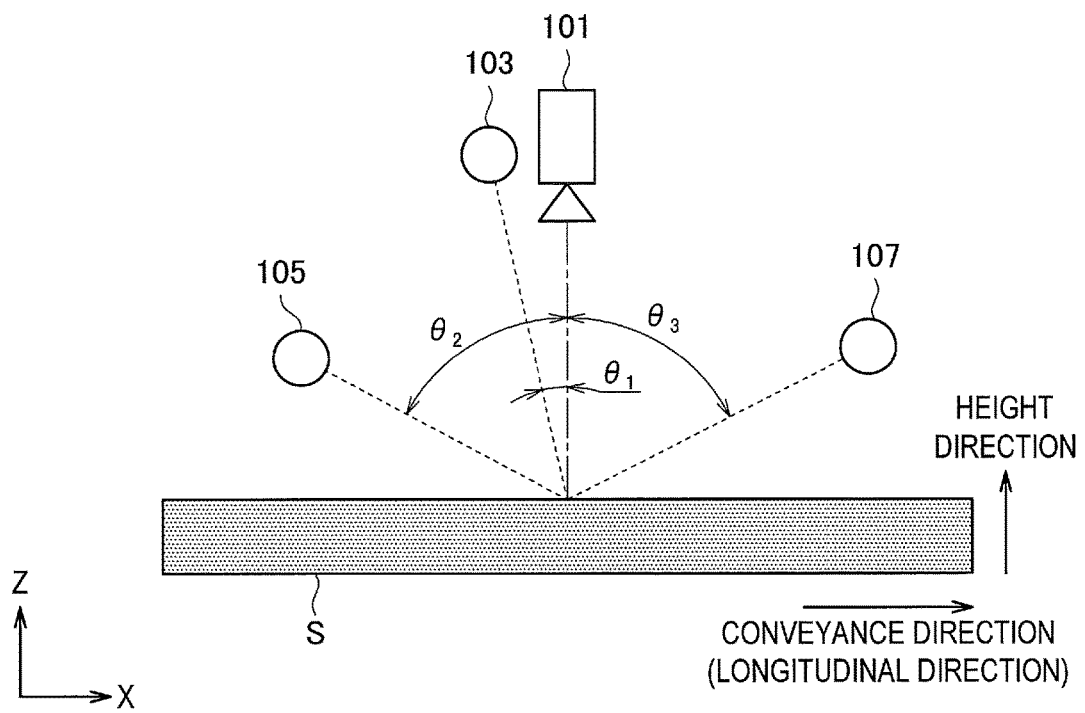
FIG. 7 is an explanatory view schematically showing a configuration example of a measurement apparatus included in a surface state monitoring apparatus according to a second embodiment of the present invention, and shows a state in which a metallic body is viewed from a side face.

Next, with reference to FIG. 7, a configuration and a function of a surface state monitoring apparatus according to a second embodiment of the present invention will be described. FIG. 7 is an explanatory view schematically showing a configuration example of a measurement apparatus included in the surface state monitoring apparatus according to the present embodiment, and shows a state in which a metallic body S is viewed from a side face.

Compared to the surface state monitoring apparatus 10 according to the first embodiment, arrangement of three illumination light sources is different in the surface state monitoring apparatus according to the present embodiment. Hereinafter, description will be mainly made on a configuration of a measurement apparatus of the surface state monitoring apparatus according to the present embodiment, which is different from the first embodiment. Note that, detailed description of the same configuration and function as the first embodiment, such as the arithmetic processing apparatus of the surface state monitoring apparatus that is the same as the first embodiment, will be omitted.

[2-1. Configuration of Measurement Apparatus]

The measurement apparatus according to the present embodiment includes, as shown in FIG. 7, a color line sensor camera 101, a first illumination light source 103, a second illumination light source 105, and a third illumination light source 107. The color line sensor camera 101, the first illumination light source 103, the second illumination light source 105, and the third illumination light source 107 are fixed with a known method in a manner that the setting positions are stationary.

(Color Line Sensor Camera)

The color line sensor camera 101 is an imaging apparatus that images an image on a one-dimensional line basis. As the color line sensor camera 101, a known 3CCD color line sensor camera can be used, for example. The color line sensor camera 101 can individually and simultaneously measure magnitudes of various wavelength components (for example, an R component, a G component, and a B component) included in reflected light beams of a first illumination light beam, a second illumination light beam, and a third illumination light beam.

The color line sensor camera 101 is provided in a manner that the optical axis of the color line sensor camera 101 is perpendicular to the metallic body surface above the metallic body S (side in the positive direction of the Z-axis). The color line sensor camera 101 measures separately reflected light beams of the first illumination light beam emitted from the first illumination light source 103, the second illumination light beam emitted from the second illumination light source 105, and the third illumination light beam emitted from the third illumination light source 107, which are reflected on the metallic body surface. In this way, the color line sensor camera 101 can specify data indicating intensities of reflected light beams of the first illumination light beam, the second illumination light beam, and the third illumination light beam reflected on the metallic body surface (that is, data indicating luminance values of the reflected light beams). As a result of the color line sensor camera 101 imaging the metallic body surface every time the metallic body S is conveyed a certain distance, for example, the color line sensor camera 101 can specify distribution in a conveyance direction and a width direction (in the XY-plane of FIG. 1) of each of the reflected light of the first illumination light on the metallic body surface, the reflected light of the second illumination light on the metallic body surface, and the reflected light of the third illumination light on the metallic body surface.

The color line sensor camera 101 measures separately the respective luminance values of the reflected light beams of the first illumination light beam, the second illumination light beam, and the third illumination light beam, generates data corresponding to the acquired measurement results (data on the luminance values of the reflected light beams), and outputs the data to the arithmetic processing apparatus 200 to be described later.

(Illumination Light Source)

In the same manner as the first embodiment, the measurement apparatus according to the present embodiment includes three illumination light sources, the first illumination light source 103, the second illumination light source 105, and the third illumination light source 107. The illumination light sources 103, 105, and 107 irradiate the surface of the metallic body S with, the first illumination light, the second illumination light, and the third illumination light, respectively.

In the present embodiment, the first illumination light source 103 is provided for obtaining second information on surface roughness of the metallic body S. The wavelength of the first illumination light source 103 is selected from the wavelength band range corresponding to a hue monitored from the metallic body surface. In this way, the variation in surface roughness can be monitored with high accuracy in a state hardly influenced by variation in hue occurred on the metallic body surface.

Further, the first illumination light source 103 is disposed in a manner that the degrees of an angle (first angle: $\theta_1$) between the optical axis of the first illumination light source 103 and the optical axis of the color line sensor camera 101 is as small as possible as long as there is no constraint on light sources installation. For example, the first angle $\theta_1$ is set to more than or equal to 3° and less than or equal to 30°. In this way, the color line sensor camera 101 can acquire the reflected light of the first illumination light as specular reflection measurement data that is near the specular reflection. Since the data measured under the condition near the specular reflection clearly exhibits variation in surface roughness on the metallic body, the variation in surface roughness can be monitored with high sensitivity.

On the other hand, in the present embodiment, the second illumination light source 105 and the third illumination light source 107 are provided for acquiring first information on a hue of the metallic body S. The wavelength of the second illumination light source 105 and the wavelength of the third illumination light source 107 are each selected from the wavelength band range corresponding to a complementary color of a hue monitored from the metallic body surface using the first illumination light source 103. In this case, the wavelength of the second illumination light source 105 and the wavelength of the third illumination light source 107 are different from each other. In this way, the variation in hue that occurs on the metallic body surface can be monitored with high accuracy.

Further, the second illumination light source 105 and the third illumination light source 107 are disposed in a manner that the illumination light beams are incident on the metallic body surface at low angles. To be specific, as shown in FIG. 7, the second illumination light source 105 and the third illumination light source 107 are provided symmetrically about the optical axis of the color line sensor camera 101. That is, where an angle (second angle) between the optical axis of the second illumination light source 105 and the optical axis of the color line sensor camera 101 is represented by $\theta_2$, and an angle (third angle) between the optical axis of the third illumination light source 107 and the optical axis of the color line sensor camera 101 is represented by $\theta_3$, the second angle $\theta_2$ and the third angle $\theta_3$ are substantially equal to each other.

In this case, the second angle $\theta_2$ and the third angle $\theta_3$ are each set to more than or equal to 3° and less than or equal to 30°, for example. In this way, the color line sensor camera 101 can acquire the reflected light of the second illumination light and the reflected light of the third illumination light as diffused reflection measurement data having a small amount of the specular reflection component. Since the data measured at a position distant from the specular reflection exhibits a "color density (that is, chroma)" strongly, the contrast in the image can be increased, and as a result, the sensitivity of the monitoring of hue variation can be increased. Note that the second angle $\theta_2$ and the third angle $\theta_3$ are each set to an angle larger than the first angle $\theta_1$.

With the above configuration of the measurement apparatus, in the same manner as the first embodiment, the color line sensor camera 101 measures reflected light beams of the respective illumination light beams, which are reflected on the metallic body surface. In this way, pieces of data indicating intensities of reflected light beams of the first illumination light beam, the second illumination light beam, and the third illumination light beam reflected on the metallic body surface (that is, data indicating luminance values of the reflected light beams) can each be specified. As a result of the color line sensor camera 101 imaging the metallic body surface every time the metallic body S is conveyed a certain distance, for example, the color line sensor camera 101 can specify distribution in a conveyance direction and a width direction (in the XY-plane of FIG. 1) of each of the reflected light of the first illumination light on the metallic body surface, the reflected light of the second illumination light on the metallic body surface, and the reflected light of the third illumination light on the metallic body surface.

The color line sensor camera 101 measures separately the respective luminance values of the reflected light beams of the first illumination light beam, the second illumination light beam, and the third illumination light beam, generates data corresponding to the acquired measurement results (data on the luminance values of the reflected light beams), and outputs the data to the arithmetic processing apparatus 200 in the same manner as in the first embodiment. The arithmetic processing apparatus 200 monitors the state of the metallic body surface on the basis of the thus obtained respective pieces of measurement data. The processing performed by the arithmetic processing apparatus 200 may be basically the same as the first embodiment.

Note that, in multiplying at least one of the measurement data of the second illumination light and the measurement data of the third illumination light by a predetermined coefficient and then calculating the sum of the measurement data of the second illumination light and the measurement data of the third illumination light, it differs from the first embodiment. A value of a constant may be determined in advance in a manner that the difference is the largest between: the value of the sum of the measurement data of the second illumination light and the measurement data of the third illumination light measured at a region in which an abnormal portion having a specific hue occurs; and the value of the sum of the measurement data of the second illumination light and the measurement data of the third illumination light measured at a region in which the abnormal portion does not occur.

In the case where there is variation in the hue on the metallic body surface, variation occurs in the sum of the luminance values of the reflected light of the second illumination light and the reflected light of the third illumination light. Further, with the reflected light of the first illumination light, variation in surface roughness can be monitored with high sensitivity in a state hardly influenced by variation in hue on the metallic body surface.

Heretofore, the configuration of the measurement apparatus according to the present embodiment has been described. Note that, although the case has been described in FIG. 7 in which the first illumination light source 103 is provided on the upstream side of the conveyance direction, the present invention is not limited to such an example. For example, the first illumination light source 103 may be provided on the downstream side of the conveyance direction. Further, although the case has been described in FIG. 7 in which the first illumination light source 103 and the second illumination light source 105 are provided on the upstream side of the conveyance direction, and the third illumination light source 107 is provided on the downstream side of the conveyance direction, the present invention is not limited to such an example. For example, the third illumination light source 107 may be provided on the upstream side of the conveyance direction and the first illumination light source 103 and the second illumination light source 105 may be provided on the downstream side of the conveyance direction.

[2-2. Conclusion]

According to the surface state monitoring apparatus according to the second embodiment, the surface of the metallic body S is irradiated with three illumination light beams and the color line sensor camera measures reflected light beams of the respective illumination light beams.

The first illumination light source 103 is a light source that emits light of a wavelength belonging to a wavelength band range corresponding to a hue monitored from the metallic body surface, and is provided in a manner that the illumination light is incident on the metallic body surface at a high angle. Such a first illumination light source 103 is provided in the above-mentioned manner, and the second information on surface roughness of the metallic body S can be acquired from the measurement data of the first illumination light acquired by the color line sensor camera 101, which is provided so as to be substantially parallel to a normal direction of the surface of the metallic body S.

Further, the second illumination light source 105 and the third illumination light source 107 are each a light source that emits light of a wavelength belonging to a wavelength band range corresponding to a complementary color of a hue monitored from the metallic body surface, and are provided in a manner that the illumination light beams are incident on the metallic body surface at low angles. Such second illumination light source 105 and third illumination light source 107 are provided in the above-mentioned manner, and the first information on a hue of the surface of the metallic body S can be acquired from the measurement data of the second illumination light and the measurement data of the third illumination light acquired by the color line sensor camera 101.

3. Hardware Configuration

Figure 8:
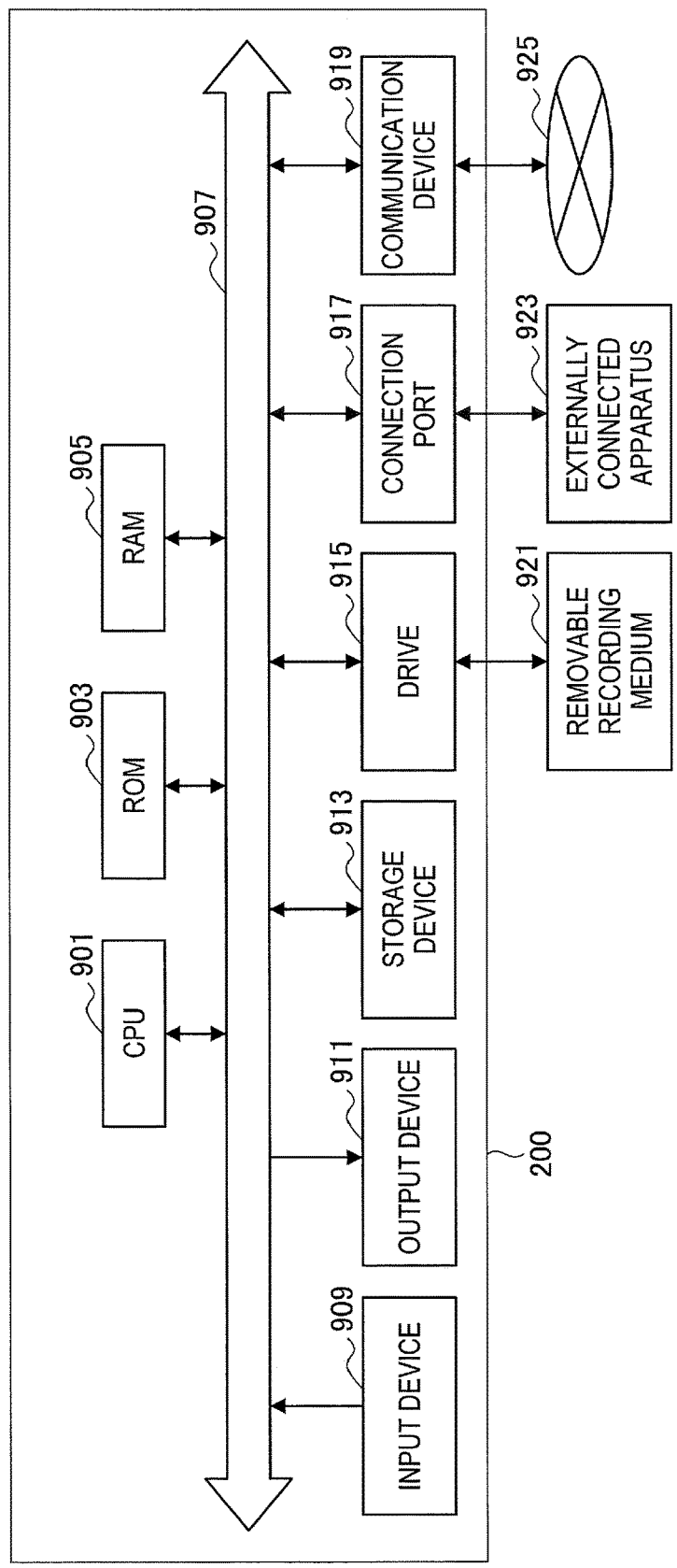
FIG. 8 is a block diagram showing a hardware configuration of an arithmetic processing apparatus according to each embodiment of the present invention.

With reference to FIG. 8, a hardware configuration of the arithmetic processing apparatus 200 according to the above embodiments of the present invention will be described in detail. FIG. 8 is a block diagram showing the hardware configuration of the arithmetic processing apparatus 200 according to each embodiment of the present invention.

The arithmetic processing apparatus 200 mainly includes a CPU 901, a ROM 903, and a RAM 905. Furthermore, the arithmetic processing apparatus 200 also includes a bus 907, an input device 909, an output device 911, a storage device 913, a drive 915, a connection port 917, and a communication device 919.

The CPU 901 serves as an arithmetic processing apparatus and a control device, and controls the overall operation or a part of the operation of the arithmetic processing apparatus 200 according to various programs recorded in the ROM 903, the RAM 905, the storage device 913, or a removable recording medium 921. The ROM 903 stores programs, operation parameters, and the like used by the CPU 901. The RAM 905 primarily stores programs that the CPU 901 uses and parameters and the like varying as appropriate during the execution of the programs. These are connected with each other via the bus 907 configured from an internal bus such as a CPU bus or the like.

The bus 907 is connected to the external bus such as a PCI (Peripheral Component Interconnect/Interface) bus via the bridge.

The input device 909 is an operation means operated by a user, such as a mouse, a keyboard, a touch panel, buttons, a switch, and a lever. The input device 909 may be a remote control means (a so-called remote control) using, for example, infrared light or other radio waves, or may be an externally connected apparatus 923 such as a PDA conforming to the operation of the arithmetic processing apparatus 200. Furthermore, the input device 909 generates an input signal based on, for example, information which is input by a user with the above operation means, and is configured from an input control circuit for outputting the input signal to the CPU 901. The user can input various data to the surface state monitoring apparatus 10 and can instruct the surface state monitoring apparatus 10 to perform processing by operating this input device 909.

The output device 911 is configured from a device capable of visually or audibly notifying acquired information to a user. Examples of such device include display devices such as a CRT display device, a liquid crystal display device, a plasma display device, an EL display device, and lamps, audio output devices such as a speaker and a headphone, a printer, a mobile phone, a facsimile machine, and the like. For example, the output device 911 outputs a result obtained by various processes performed by the arithmetic processing apparatus 200. More specifically, the display device displays, in the form of texts or images, a result obtained by various processes performed by the arithmetic processing apparatus 200. On the other hand, the audio output device converts an audio signal such as reproduced audio data and sound data into an analog signal, and outputs the analog signal.

The storage device 913 is a device for storing data configured as an example of a storage unit of the arithmetic processing apparatus 200 and is used to store data. The storage device 913 is configured from, for example, a magnetic storage device such as a HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for recording medium, and is embedded in the arithmetic processing apparatus 200 or attached externally thereto. The drive 915 reads information recorded in the attached removable recording medium 921 such as a magnetic disk, an optical disc, a magneto-optical disk, or a semiconductor memory, and outputs the read information to the RAM 905. Furthermore, the drive 915 can write in the attached removable recording medium 921 such as a magnetic disk, an optical disc, a magneto-optical disk, or a semiconductor memory. The removable recording medium 921 is, for example, a CD medium, a DVD medium, or a Blu-ray (registered trademark) medium. The removable recording medium 921 may be a CompactFlash (CF; registered trademark), a flash memory, an SD memory card (Secure Digital Memory Card), or the like. Alternatively, the removable recording medium 921 may be, for example, an IC card (Integrated Circuit Card) equipped with a non-contact IC chip or an electronic device.

The connection port 917 is a port for allowing devices to directly connect to the arithmetic processing apparatus 200. Examples of the connection port 917 include a USB (Universal Serial Bus) port, an IEEE1394 port, a SCSI (Small Computer System Interface) port, an RS-232C port, and the like. By the externally connected apparatus 923 connecting to this connection port 917, the arithmetic processing apparatus 200 directly obtains various data from the externally connected apparatus 923 and provides various data to the externally connected apparatus 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the arithmetic processing apparatus 200 according to an embodiment of the present invention has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

EXAMPLES

Hereinafter, with reference to specific examples, the surface state monitoring apparatus 10 according to the above embodiments of the present invention will be described. Examples shown below are merely examples of the surface state monitoring apparatus and the surface state monitoring method according to the present invention. The surface state monitoring apparatus and the surface state monitoring method according to the present invention are not limited to Examples shown below.

Example 1: Monitoring of Yellowing and Surface Roughness Variation in Pickling Step In Example 1, monitoring of yellowing and surface roughness variation in a pickling step will be described. The pickling step is a process of immersing a steel plate in an acidic solution of hydrochloric acid, sulfuric acid, or the like, then taking out the steel plate in the air, and washing the steel plate with pure water or hot water, which is performed as a process of removing scale from a hot-rolled coil or as a plating preprocess for a steel strip in coil. If the washing with water is not performed immediately after being immersed in the acidic solution, there occurs yellow rust on a surface of the steel plate caused by adhesion of the acidic solution to the surface. The occurrence of the yellow rust is referred to as yellowing.

The yellowing is an abnormality of the surface state that appears in a sheet shape as a region having a yellow hue on the steel plate surface. In the case where the yellowing is monitored by the surface state monitoring apparatus 10 according to the first embodiment, used as the first illumination light source 103 is a blue illumination light source having a wavelength near a complementary color of the yellowing. In this case, the blue illumination light source is disposed in a manner that the reflected light of the illumination light emitted from the illumination light source is measured by a corresponding line sensor camera as diffused reflection measurement data, and that the illumination light is incident on the steel plate at a low angle. In this way, the color density to be measured increases and the contrast in an image to be acquired increases, and hence, it becomes easier to monitor the yellowing.

On the other hand, depending on the concentration of the pickling solution used in the pickling step, variation in the roughness of the steel plate surface occurs. For example, in the case where a highly concentrated pickling solution is used, rough skin easily occurs on the steel plate surface due to overpickling. On the other hand, in the case where a low concentrated pickling solution is used, a scale residue easily occurs due to insufficient pickling. In the surface state monitoring apparatus 10 according to the above embodiment, such a region with no specific hue in which surface roughness varies is monitored using pieces of measurement data of the respective illumination light beams of the second illumination light source 105 and the third illumination light source 107.

In this case, in order that the monitoring can be performed even in the case where a region in which surface roughness varies is present in the region having a yellow hue such as the yellowing, the second illumination light source 105 and the third illumination light source 107 use, illumination light sources other than the blue illumination light source used for the first illumination light source 103, that is, a red illumination light source and a green illumination light source. The red illumination light source and the green illumination light source are disposed in a manner that the reflected light beams of the illumination light beams emitted from those illumination light sources are measured by a color line sensor camera as specular reflection measurement data, and that the illumination light is incident on the steel plate at a high angle. The arithmetic processing apparatus 200 uses the specular reflection measurement data to calculate the sum of the luminance of the red component and the luminance of the green component, and, by adjusting a predetermined coefficient used in calculating the sum in the above-mentioned manner, a state is made that is hardly influenced by hues appeared on the steel plate surface. Further, by using the specular reflection measurement data that enables the monitoring of variation in surface roughness with high sensitivity, rough skin and scale residue can be monitored with high accuracy.

As an example, measurement is performed on a steel plate sample on which yellowing and scale residue occur at a same location using the surface state monitoring apparatus 10 for a metallic body according to the first embodiment. In this case, the three illumination light sources are provided as shown in FIG. 2, in a manner that a distance between the steel plate and each illumination light source is 400 mm, a width of each illumination light source (length in the longitudinal direction) is 800 mm, and an illumination width of each illumination light beam on the steel plate is approximately 10 to 30 mm. The first illumination light source is blue, and the second illumination light source and the third illumination light source are red and green. An angle of incidence ($\theta_1$) of the illumination light emitted from the blue illumination light source is set to 60°, and an angle of incidence ($\theta_2$) of the illumination light emitted from the red illumination light source and an angle of incidence ($\theta_3$) emitted from the green illumination light source are each set to 10° with the color line sensor camera therebetween, the color line sensor camera being provided so as to be substantially parallel to a normal direction of the steel plate surface. The color line sensor camera is a CMOS color line sensor camera, and a distance between the color line sensor camera and the steel plate surface is set to 500 mm.

Figure 9:
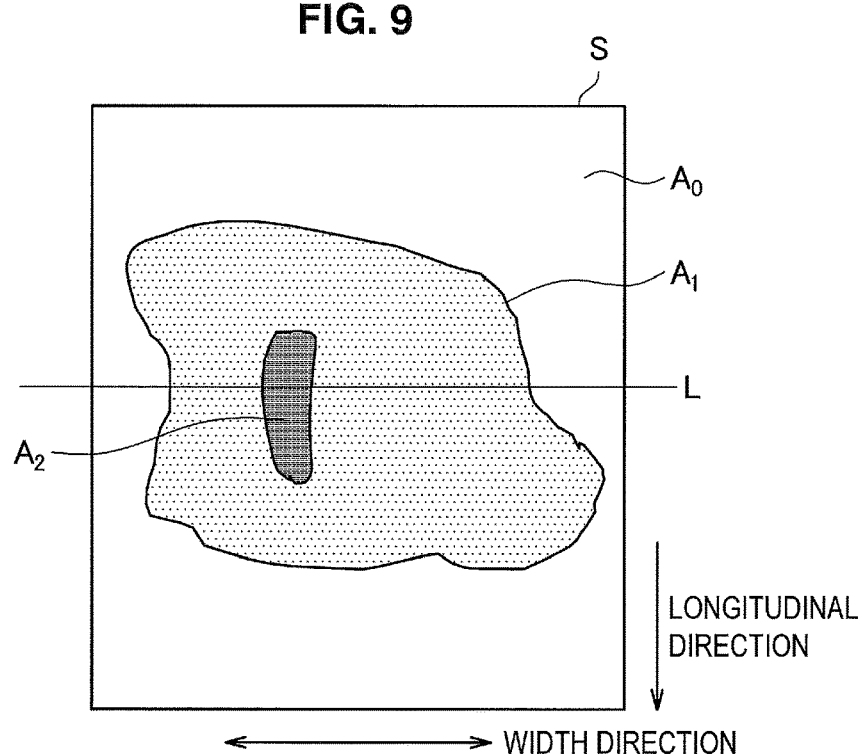
FIG. 9 is an explanatory view showing an example of a hue-varied region and a roughness-varied region specified by an image for monitoring hue variation and an image for monitoring roughness variation acquired by an arithmetic processing apparatus.
Figure 9:
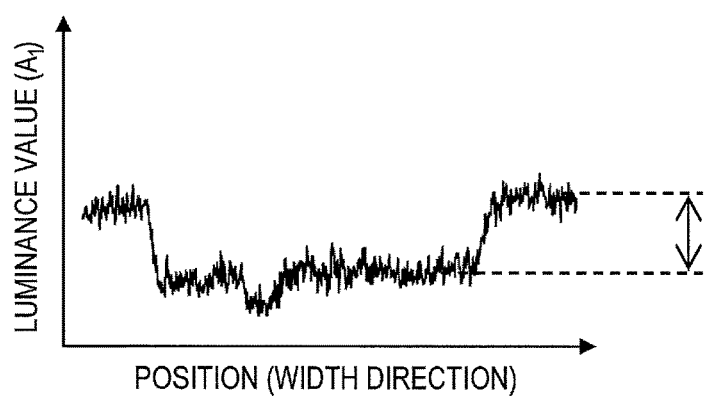
Figure 9:
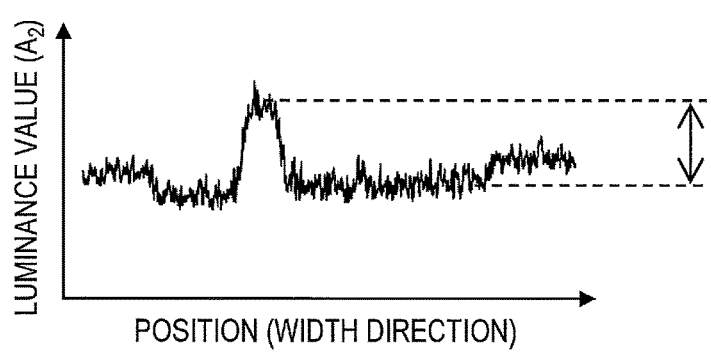

FIG. 9 shows an example of a hue-varied region in which hue variation occurs and a roughness-varied region in which roughness variation occurs specified by an image for monitoring hue variation and an image for monitoring roughness variation acquired by the arithmetic processing apparatus 200.

The upper part of FIG. 9 shows a diagram in which pieces of binary-converted data of the image for monitoring hue variation and the image for monitoring roughness variation are superimposed on each other. In FIG. 9, a region $A_0$ represents a portion determined to be a normal region which is free of surface abnormality. A region $A_1$ represents a region specified as a hue-varied region, which is a region in which yellowing occurs in the present example. A region $A_2$ represents a region specified as a roughness-varied region, which is a region in which scale residue occurs in the present example.

For each of the image for monitoring hue variation and the image for monitoring roughness variation, a luminance profile is produced for showing variation in luminance values in the width direction at a predetermined position in the longitudinal direction of the steel plate. The lower part of FIG. 9 shows the luminance profile along a line L.

First, the middle part of FIG. 9 shows a luminance profile along the line L of a captured image obtained from the first illumination light source 103. Here, since the first illumination light source 103 uses a blue illumination light source having a wavelength near a complementary color of yellowing, it is expected that the region $A_1$ in which the yellowing occurs can be monitored. It can be seen from the luminance profile along the line L regarding the first illumination light source 103 that the luminance values at the edge portions in the width direction of the steel plate are actually high and the luminance values at the central portion in the width direction of the steel plate are actually low. Thus, it can be understood that the normal region $A_0$ and the hue-varied region $A_1$ shown in the upper part of FIG. 9 can be clearly distinguished from each other. That is, the region in which variation in hue occurs can be monitored with high accuracy.

Further, the lower part of FIG. 9 shows a luminance profile along the line L of a luminance image acquired on the basis of the sum of a luminance value obtained from the second illumination light source 105 and a luminance value obtained from the third illumination light source 107. Here, since the luminance image acquired on the basis of the sum of the luminance value obtained from the second illumination light source 105 and the luminance value obtained from the third illumination light source 107 has a predetermined coefficient that has been adjusted as described above, it is expected that the roughness-varied region $A_2$ can be monitored in a state hardly influenced by yellowing. It can be seen from the luminance profile along the line L of the luminance image acquired on the basis of the sum of the luminance value obtained from the second illumination light source 105 and the luminance value obtained from the third illumination light source 107 that there is actually a part near the center of the steel plate in which the luminance values are remarkably high. Thus, it can be understood that the normal region $A_0$ and the roughness-varied region $A_2$ shown in the upper part of FIG. 9 can be clearly distinguished from each other. Here, although the roughness-varied region $A_2$ is placed inside the hue-varied region $A_1$, in the luminance profile of the region $A_2$, the luminance values at the portions other than the roughness-varied region $A_2$ are low, regardless of whether the roughness-varied region $A_2$ is placed inside or outside of the hue-varied region $A_1$. Therefore, the region in which variation in surface roughness occurs can be monitored with high accuracy in a state hardly influenced by variation in hue.

Note that, although the distance between the steel plate and each illumination light source has been set to 400 mm in the present example, the distance may be set to approximately 200 to 500 mm. Further, the width of each illumination light source (length in the longitudinal direction) is determined in accordance with a measurement target, and may be set to approximately 800 to 2000 mm, for example. Still further, the distance between the color line sensor camera and the steel plate surface may be set to approximately 200 to 1000 mm.

Example 2: Monitoring of Temper Color and Surface Roughness Variation in Stainless Steel Production Step In Example 2, there will be described a case where the surface state monitoring apparatus according to the second embodiment performs monitoring of a temper color and a surface state in a stainless steel production step.

By undergoing an annealing step of subjecting a hot rolled-annealed-pickled plate or a hot rolled-pickled plate to 70 to 90% cold rolling and then causing a cold worked structure to be recrystallized through final heat treatment, the structure of a stainless steel plate is made uniform. Such an annealing step is performed while controlling an atmosphere in an annealing furnace, however, the control of the atmosphere in the annealing furnace may become unstable at the beginning of product production, or the control itself of the annealing atmosphere may fail. In the case where the atmosphere control becomes unstable or the failure occurs in the control, an oxide film is generated on a surface of the annealed material. The oxide film is formed on a surface of the stainless steel. The oxide film is different from a passivation film in which chromium (Cr) is concentrated, and has decreased Cr concentration and a large amount of iron (Fe) concentrated therein. Further, the oxide film shows a temper color which varies between gold, blue, reddish purple, and the like in accordance with an interference effect of light which is attributed to a thickness and a refractive index of the film.

The temper color in the stainless steel production step is an abnormality of the surface state that appears in a sheet shape as a region having a predetermined hue on the steel plate surface. In the present example, a region in which the temper color does not have a specific hue and surface roughness varies is monitored using measurement data of the illumination light emitted from the first illumination light source 103. A blue illumination light source is used for the first illumination light source 103 in order that the monitoring can be performed also in the case where a region in which surface roughness varies is present in a region in which a blue temper color is shown. The blue illumination light source is disposed in a manner that the reflected light of the illumination light emitted from the blue illumination light source is measured by the color line sensor camera 101 as specular reflection measurement data and in a manner that the illumination light is incident on the steel plate at a high angle. In this way, using the reflected light of the illumination light emitted from the blue illumination light source as the measurement data, variation in surface roughness can be monitored with high sensitivity in a state hardly influenced by variation in hue appeared on the steel plate surface.

On the other hand, a region in which the temper color has a specific hue is monitored using measurement data of the illumination light beams emitted from the second illumination light source 105 and the third illumination light source 107. Green and red illumination light sources are used for the illumination light beams emitted from the second illumination light source 105 and the third illumination light source 107, respectively. In this case, the green and red illumination light sources are disposed in a manner that the reflected light beams of the illumination light beams emitted from the respective illumination light sources are measured by the color line sensor camera as pieces of diffused reflection measurement data, and in a manner that the illumination light beams are incident on the steel plate at low angles. In this way, the color density to be measured increases and the contrast in an image to be acquired increases, and hence, it becomes easier to monitor the blue temper color.

Note that, in the case of performing particularly monitoring a reddish purple temper color in the situation in which a temper color which is not blue but which is near reddish purple occurs, a red illumination light source having a wavelength near reddish purple can also be used as the first illumination light source 103. In this case, green and blue illumination light sources are used for the second illumination light source 105 and the third illumination light source 107, respectively. In this way, it becomes easier to monitor the reddish purple temper color.

The preferred embodiments of the present invention have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 10 surface state monitoring apparatus
100 measurement apparatus
101 color line sensor camera
103 first illumination light source
105 second illumination light source
107 third illumination light source
200 arithmetic processing apparatus
201 data acquisition unit
203 measurement control unit
205 data processing unit
207 display control unit
209 storage unit
221 measurement value preprocessing unit
223 measurement value processing unit
225 surface state determination unit
229 feature quantity extraction unit
231 determination unit
233 result output unit

The invention claimed is:

1. A surface state monitoring apparatus configured to determine a surface state of a metallic body,
the surface state monitoring apparatus comprising:
a first illumination light source configured to irradiate a surface of the metallic body with a first illumination light beam having a strip shape;
a second illumination light source configured to irradiate the surface of the metallic body with a second illumination light beam having a strip shape;
a third illumination light source configured to irradiate the surface of the metallic body with a third illumination light beam having a strip shape;
a color line sensor camera configured to measure separately reflected light beams at the surface of the metallic body of the three illumination light beams; and
an arithmetic processing apparatus configured to calculate surface state monitoring information used for monitoring the surface state of the metallic body on the basis of luminance values of the reflected light beams measured by the color line sensor camera, wherein
the color line sensor camera is provided in a manner that an optical axis of the color line sensor camera is substantially parallel to a normal direction of the surface of the metallic body,
the second illumination light source and the third illumination light source are provided in a manner that a second angle between the optical axis of the color line sensor camera and an optical axis of the second illumination light source is substantially equal to a third angle between the optical axis of the color line sensor camera and an optical axis of the third illumination light source,
the first illumination light source is provided in a manner that a first angle between the optical axis of the color line sensor camera and an optical axis of the first illumination light source is different from the second angle and the third angle,
the first illumination light source, the second illumination light source, and the third illumination light source are provided in a manner that the first angle is larger than the second angle and the third angle, and
the arithmetic processing apparatus
calculates, as the surface state monitoring information, first information on a hue of the surface of the metallic body and second information on surface roughness of the metallic body, on the basis of the luminance value of the reflected light beam of the first illumination light beam, the luminance value of the reflected light beam of the second illumination light beam, and the luminance value of the reflected light beam of the third illumination light beam, and
determines the surface state of the metallic body on the basis of the first information on the hue of the surface of the metallic body and the second information on the surface roughness of the metallic body.

2. A surface state monitoring apparatus configured to determine a surface state of a metallic body,
the surface state monitoring apparatus comprising:
a first illumination light source configured to irradiate a surface of the metallic body with a first illumination light beam having a strip shape and a color near to a complementary color of a hue of an abnormal portion of the surface of the metallic body among red, green, and blue, which are three primary colors of light;
a second illumination light source configured to irradiate the surface of the metallic body with a second illumination light beam having a strip shape and a color different from the color of the first illumination light beam among red, green, and blue, which are the three primary colors of light;
a third illumination light source configured to irradiate the surface of the metallic body with a third illumination light beam having a strip shape and a color different from the colors of the first illumination light beam and the second illumination light beam among red, green, and blue, which are the three primary colors of light;

a color line sensor camera configured to measure separately reflected light beams at the surface of the metallic body of the three illumination light beams; and an arithmetic processing apparatus configured to calculate surface state monitoring information used for monitoring the surface state of the metallic body on the basis of luminance values of the reflected light beams measured by the color line sensor camera, wherein the color line sensor camera is provided in a manner that an optical axis of the color line sensor camera is substantially parallel to a normal direction of the surface of the metallic body, the second illumination light source and the third illumination light source are provided in a manner that a second angle between the optical axis of the color line sensor camera and an optical axis of the second illumination light source is substantially equal to a third angle between the optical axis of the color line sensor camera and an optical axis of the third illumination light source, the first illumination light source is provided in a manner that a first angle between the optical axis of the color line sensor camera and an optical axis of the first illumination light source is different from the second angle and the third angle, and the arithmetic processing apparatus calculates, as the surface state monitoring information, first information on a hue of the surface of the metallic body and second information on surface roughness of the metallic body, on the basis of the luminance value of the reflected light beam of the first illumination light beam, the luminance value of the reflected light beam of the second illumination light beam, and the luminance value of the reflected light beam of the third illumination light beam, and determines the surface state of the metallic body on the basis of the first information on the hue of the surface of the metallic body and the second information on the surface roughness of the metallic body.

3. The surface state monitoring apparatus according to claim 2, wherein the first illumination light source is provided in a manner that the color line sensor camera can measure the reflected light beam at the surface of the metallic body of the first illumination light beam at a position distant from a specular direction, the second illumination light source and the third illumination light source are provided in a manner that the color line sensor camera can measure the reflected light beams at the surface of the metallic body of the second illumination light beam and the third illumination light beam at a position near to specular directions, and the first illumination light source, the second illumination light source, and the third illumination light source are provided in a manner that the first angle is larger than the second angle and the third angle.

4. The surface state monitoring apparatus according to claim 3, wherein an angle between the optical axis of the color line sensor camera and the normal direction of the surface of the metallic body is less than or equal to 5°, the first angle is more than or equal to 45°, and the second angle and the third angle are each more than or equal to 3° and less than or equal to 30°.

5. A surface state monitoring apparatus configured to determine a surface state of a metallic body, the surface state monitoring apparatus comprising:

a second illumination light source configured to irradiate a surface of the metallic body with a second illumination light beam having a strip shape and a color near to a complementary color of a hue of an abnormal portion of the surface of the metallic body among red, green, and blue, which are three primary colors of light;

a third illumination light source configured to irradiate the surface of the metallic body with a third illumination light beam having a strip shape and a color that is different from the color of the second illumination light beam among red, green, and blue, which are the three primary colors of light, and is near to the complementary color of the hue of the abnormal portion of the surface of the metallic body;

a first illumination light source configured to irradiate the surface of the metallic body with a first illumination light beam having a strip shape and a color different from the colors of the second illumination light beam and the third illumination light beam among red, green, and blue, which are the three primary colors of light;

a color line sensor camera configured to measure separately reflected light beams at the surface of the metallic body of the three illumination light beams; and an arithmetic processing apparatus configured to calculate surface state monitoring information used for monitoring the surface state of the metallic body on the basis of luminance values of the reflected light beams measured by the color line sensor camera, wherein the color line sensor camera is provided in a manner that an optical axis of the color line sensor camera is substantially parallel to a normal direction of the surface of the metallic body, the second illumination light source and the third illumination light source are provided in a manner that a second angle between the optical axis of the color line sensor camera and an optical axis of the second illumination light source is substantially equal to a third angle between the optical axis of the color line sensor camera and an optical axis of the third illumination light source, the first illumination light source is provided in a manner that a first angle between the optical axis of the color line sensor camera and an optical axis of the first illumination light source is different from the second angle and the third angle, and the arithmetic processing apparatus calculates, as the surface state monitoring information, first information on a hue of the surface of the metallic body and second information on surface roughness of the metallic body, on the basis of the luminance value of the reflected light beam of the first illumination light beam, the luminance value of the reflected light beam of the second illumination light beam, and the luminance value of the reflected light beam of the third illumination light beam, and determines the surface state of the metallic body on the basis of the first information on the hue of the surface of the metallic body and the second information on the surface roughness of the metallic body.

6. The surface state monitoring apparatus according to claim 5, wherein the first illumination light source is provided in a manner that the color line sensor camera can measure the reflected light beam at the surface of the metallic body of the first illumination light beam at a position near to a specular direction, the second illumination light source and the third illumination light source are provided in a manner that the color line sensor camera can measure the reflected light beams at the surface of the metallic body of the second illumination light beam and the third illumination light beam at a position distant from specular directions, and the first illumination light source, the second illumination light source, and the third illumination light source are provided in a manner that the first angle is smaller than the second angle and the third angle.

7. The surface state monitoring apparatus according to claim 6, wherein an angle between the optical axis of the color line sensor camera and the normal direction of the surface of the metallic body is less than or equal to 5°, the first angle is more than or equal to 3° and less than or equal to 30°, and the second angle and the third angle are each more than or equal to 45°.

8. A surface state monitoring method for determining a surface state of a metallic body, the method being performed by using a surface state monitoring apparatus including a first illumination light source configured to irradiate a surface of the metallic body with a first illumination light beam having a strip shape, a second illumination light source configured to irradiate the surface of the metallic body with a second illumination light beam having a strip shape, a third illumination light source configured to irradiate the surface of the metallic body with a third illumination light beam having a strip shape, a color line sensor camera configured to measure separately reflected light beams at the surface of the metallic body of the illumination light beams of three different colors, and an arithmetic processing apparatus configured to calculate surface state monitoring information used for monitoring the surface state of the metallic body on the basis of luminance values of the reflected light beams measured by the color line sensor camera, in which the color line sensor camera is provided in a manner that an optical axis of the color line sensor camera is substantially parallel to a normal direction of the surface of the metallic body, the second illumination light source and the third illumination light source are provided in a manner that a second angle between the optical axis of the color line sensor camera and an optical axis of the second illumination light source is substantially equal to a third angle between the optical axis of the color line sensor camera and an optical axis of the third illumination light source, the first illumination light source is provided in a manner that a first angle between the optical axis of the color line sensor camera and an optical axis of the first illumination light source is different from the second angle and the third angle, and the first illumination light source, the second illumination light source, and the third illumination light source are provided in a manner that the first angle is larger than the second angle and the third angle, the method comprising:

irradiating the surface of the metallic body with the illumination light beams by the first illumination light source, the second illumination light source, and the third illumination light source;

measuring separately the reflected light beams of the illumination light beams from the surface of the metallic body by the color line sensor camera;

calculating, as the surface state monitoring information, first information on a hue of the surface of the metallic body and second information on surface roughness of the metallic body, on the basis of the measured luminance value of the reflected light beam of the first illumination light beam, the measured luminance value of the reflected light beam of the second illumination light beam, and the measured luminance value of the reflected light beam of the third illumination light beam; and determining the surface state of the metallic body on the basis of the first information on the hue of the surface of the metallic body and the second information on the surface roughness of the metallic body.

9. A surface state monitoring method for determining a surface state of a metallic body, the method being performed by using a surface state monitoring apparatus including a first illumination light source configured to irradiate a surface of the metallic body with a first illumination light beam having a strip shape and a color near to a complementary color of a hue of an abnormal portion of the surface of the metallic body among red, green, and blue, which are three primary colors of light, a second illumination light source configured to irradiate the surface of the metallic body with a second illumination light beam having a strip shape and a color different from the color of the first illumination light beam among red, green, and blue, which are the three primary colors of light, a third illumination light source configured to irradiate the surface of the metallic body with a third illumination light beam having a strip shape and a color different from the colors of the first illumination light beam and the second illumination light beam among red, green, and blue, which are the three primary colors of light, a color line sensor camera configured to measure separately reflected light beams at the surface of the metallic body of the illumination light beams of three different colors, and an arithmetic processing apparatus configured to calculate surface state monitoring information used for monitoring the surface state of the metallic body on the basis of luminance values of the reflected light beams measured by the color line sensor camera, in which the color line sensor camera is provided in a manner that an optical axis of the color line sensor camera is substantially parallel to a normal direction of the surface of the metallic body, the second illumination light source and the third illumination light source are provided in a manner that a second angle between the optical axis of the color line sensor camera and an optical axis of the second illumination light source is substantially equal to a third angle between the optical axis of the color line sensor camera and an optical axis of the third illumination light source, and the first illumination light source is provided in a manner that a first angle between the optical axis of the color line sensor camera and an optical axis of the first illumination light source is different from the second angle and the third angle, the method comprising:

irradiating the surface of the metallic body with the illumination light beams by the first illumination light source, the second illumination light source, and the third illumination light source;

measuring separately the reflected light beams of the illumination light beams from the surface of the metallic body by the color line sensor camera;

calculating, as the surface state monitoring information, first information on a hue of the surface of the metallic body and second information on surface roughness of the metallic body, on the basis of the measured luminance value of the reflected light beam of the first illumination light beam, the measured luminance value of the reflected light beam of the second illumination light beam, and the measured luminance value of the reflected light beam of the third illumination light beam; and determining the surface state of the metallic body on the basis of the first information on the hue of the surface of the metallic body and the second information on the surface roughness of the metallic body.

10. The surface state monitoring method according to claim 9, wherein the first illumination light source is provided in a manner that the reflected light beam at the surface of the metallic body of the first illumination light beam can be measured at a position distant from a specular direction, the second illumination light source and the third illumination light source are provided in a manner that the reflected light beams at the surface of the metallic body of the second illumination light beam and the third illumination light beam can be measured at a position near to specular directions, and the first illumination light source, the second illumination light source, and the third illumination light source are provided in a manner that the first angle is larger than the second angle and the third angle.

11. The surface state monitoring method according to claim 10, wherein an angle between the optical axis of the color line sensor camera and the normal direction of the surface of the metallic body is less than or equal to 5°, the first angle is more than or equal to 45°, and the second angle and the third angle are each more than or equal to 3° and less than or equal to 30°.

12. A surface state monitoring method for determining a surface state of a metallic body, the method being performed by using a surface state monitoring apparatus including a second illumination light source configured to irradiate a surface of the metallic body with a second illumination light beam having a strip shape and a color near to a complementary color of a hue of an abnormal portion of the surface of the metallic body among red, green, and blue, which are three primary colors of light, a third illumination light source configured to irradiate the surface of the metallic body with a third illumination light beam having a strip shape and a color that is different from the color of the second illumination light beam among red, green, and blue, which are the three primary colors of light, and is near to the complementary color of the hue of the abnormal portion of the surface of the metallic body, a first illumination light source configured to irradiate the surface of the metallic body with a first illumination light beam having a strip shape and a color different from the colors of the second illumination light beam and the third illumination light beam among red, green, and blue, which are the three primary colors of light, a color line sensor camera configured to measure separately reflected light beams at the surface of the metallic body of the three illumination light beams, and an arithmetic processing apparatus configured to calculate surface state monitoring information used for monitoring the surface state of the metallic body on the basis of luminance values of the reflected light beams measured by the color line sensor camera, in which the color line sensor camera is provided in a manner that an optical axis of the color line sensor camera is substantially parallel to a normal direction of the surface of the metallic body, the second illumination light source and the third illumination light source are provided in a manner that a second angle between the optical axis of the color line sensor camera and an optical axis of the second illumination light source is substantially equal to a third angle between the optical axis of the color line sensor camera and an optical axis of the third illumination light source, and the first illumination light source is provided in a manner that a first angle between the optical axis of the color line sensor camera and an optical axis of the first illumination light source is different from the second angle and the third angle, the method comprising:

irradiating the surface of the metallic body with the illumination light beams by the first illumination light source, the second illumination light source, and the third illumination light source;

measuring separately the reflected light beams of the illumination light beams from the surface of the metallic body by the color line sensor camera;

calculating, as the surface state monitoring information, first information on a hue of the surface of the metallic body and second information on surface roughness of the metallic body, on the basis of the measured luminance value of the reflected light beam of the first illumination light beam, the measured luminance value of the reflected light beam of the second illumination light beam, and the measured luminance value of the reflected light beam of the third illumination light beam; and determining the surface state of the metallic body on the basis of the first information on the hue of the surface of the metallic body and the second information on the surface roughness of the metallic body.

13. The surface state monitoring method according to claim 12, wherein the first illumination light source is provided in a manner that the reflected light beam at the surface of the metallic body of the first illumination light beam can be measured at a position near to a specular direction, the second illumination light source and the third illumination light source are provided in a manner that the reflected light beams at the surface of the metallic body of the second illumination light beam and the third illumination light beam can be measured at a position distant from specular directions, and the first illumination light source, the second illumination light source, and the third illumination light source are provided in a manner that the first angle is smaller than the second angle and the third angle.

14. The surface state monitoring method according to claim 13, wherein an angle between the optical axis of the color line sensor camera and the normal direction of the surface of the metallic body is less than or equal to 5°, the first angle is more than or equal to 3° and less than or equal to 30°, and the second angle and the third angle are each more than or equal to 45°.

* * * * *